(12) United States Patent
Toy

(10) Patent No.: US 10,980,523 B1
(45) Date of Patent: Apr. 20, 2021

(54) MEDICAL DEVICE TO ACCESS PERICARDIAL SPACE WITH CONTROL

(71) Applicant: Stephanie Toy, Norwich, CT (US)

(72) Inventor: Stephanie Toy, Norwich, CT (US)

( * ) Notice: Subject to any disclaimer, the term of this patent is extended or adjusted under 35 U.S.C. 154(b) by 0 days.

(21) Appl. No.: 16/672,217

(22) Filed: Nov. 1, 2019

(51) Int. Cl.
*A61B 17/00* (2006.01)
*A61B 5/00* (2006.01)
*A61K 9/00* (2006.01)

(52) U.S. Cl.
CPC ...... *A61B 17/00234* (2013.01); *A61B 5/4839* (2013.01); *A61K 9/0019* (2013.01); *A61B 2017/00243* (2013.01); *A61B 2017/00349* (2013.01); *A61M 2202/0007* (2013.01)

(58) Field of Classification Search
CPC ............ A61B 18/1492; A61B 17/0057; A61B 17/0625; A61B 8/12; A61B 17/00234; A61B 5/4839; A61B 2017/00243; A61B 2017/00349; A61B 2017/0007; A61B 5/00; A61B 5/0002; A61B 5/0033; A61B 5/0048; A61B 5/0059; A61B 5/0093; A61F 2/2481; A61F 2/95; A61F 2/2451;
(Continued)

(56) References Cited

U.S. PATENT DOCUMENTS 4,326,569 A * 4/1982 Vaillancourt ....... A61M 39/045
138/89
4,976,688 A * 12/1990 Rosenblum ....... A61M 25/0147
604/524

(Continued)

FOREIGN PATENT DOCUMENTS

AU 2013348071 5/2014
WO WO-2016025850 A1 * 2/2016 ......... A61B 17/3478

OTHER PUBLICATIONS

Mikhail Maslov, Stephan Foianini & Mark Lovich (2017) Delivery of drugs, growth factors, genes and stem cells via intrapericardial, epicardial and intramyocardial routes for sustained local targeted therapy of myocardial disease, Expert Opinion on Drug Delivery, 14:10, 1227-1239, DOI: 10.1080/17425247.2017.1292249.
(Continued)

*Primary Examiner* — Nathan R Price
*Assistant Examiner* — Mark A Igel
(74) *Attorney, Agent, or Firm* — Hamre, Schumann, Mueller & Larson, P.C.

(57) ABSTRACT

A medical device has an outer tubular body and an inner tubular body. A tissue engagement member is attached to the distal end of the inner tubular body. The tissue engagement member and the inner tubular body are retractable inside the outer tubular body. The tip of the tissue engagement member is configured to penetrate the tissue of a patient and secure on an organ. The movement of the tissue engagement member is limited to a predetermined angle and a predetermined distance. The medical device is configured to deliver multiple agents and/or modalities through the inner tubular body. The agents and/or modalities are supplied through delivery mechanism placed inside of the inner tubular body. A method of treating cardiac condition includes applying one or more agents and/or modalities to the same area of the heart either simultaneously or sequentially.

18 Claims, 17 Drawing Sheets

(58) Field of Classification Search
CPC .......... A61F 2/013; A61F 2/966; A61N 7/02; A61M 25/04; A61K 9/0019
See application file for complete search history.

(56) References Cited

U.S. PATENT DOCUMENTS

| | | | | |
|---|---|---|---|---|
| 5,002,067 A * | 3/1991 | Berthelsen | ........... | A61N 1/0568 600/377 |
| 5,003,992 A * | 4/1991 | Holleman | ............ | A61N 1/0568 600/377 |
| 5,060,632 A * | 10/1991 | Hibino | ................. | A61B 1/0052 600/109 |
| 5,336,252 A * | 8/1994 | Cohen | ................... | A61M 25/09 606/129 |
| 5,353,800 A * | 10/1994 | Pohndorf | ............. | A61B 5/0215 600/486 |
| 5,364,351 A * | 11/1994 | Heinzelman | ...... | A61M 25/0136 600/585 |
| 5,376,094 A * | 12/1994 | Kline | ................... | A61B 17/221 606/110 |
| 5,403,311 A * | 4/1995 | Abele | ................ | A61B 18/1477 604/21 |
| 5,431,649 A * | 7/1995 | Mulier | ............... | A61B 18/1492 606/41 |
| 5,549,644 A * | 8/1996 | Lundquist | ......... | A61M 25/0136 604/22 |
| 5,556,377 A * | 9/1996 | Rosen | ............... | A61B 18/1485 604/22 |
| 5,571,088 A * | 11/1996 | Lennox | ................... | A61B 8/12 604/96.01 |
| 5,609,151 A * | 3/1997 | Mulier | ............... | A61B 18/1477 600/373 |
| 5,667,488 A * | 9/1997 | Lundquist | ................ | A61N 5/02 604/22 |
| 5,876,398 A * | 3/1999 | Mulier | ............... | A61B 18/1492 128/898 |
| 5,911,739 A * | 6/1999 | Kordis | ................. | A61B 5/0422 607/122 |
| 5,921,982 A * | 7/1999 | Lesh | ................. | A61B 18/1492 606/41 |
| 5,980,516 A * | 11/1999 | Mulier | ............... | A61B 18/1492 606/41 |
| 5,984,929 A * | 11/1999 | Bashiri | ............ | A61B 17/12154 606/108 |
| 6,013,076 A * | 1/2000 | Goble | ................ | A61B 18/1206 600/374 |
| 6,102,887 A * | 8/2000 | Altman | ............. | A61M 25/0084 604/22 |
| 6,107,699 A * | 8/2000 | Swanson | ............ | A61B 18/1492 307/112 |
| 6,254,612 B1 * | 7/2001 | Hieshima | ................... | A61F 2/88 606/108 |
| 6,428,537 B1 * | 8/2002 | Swanson | ............ | A61B 18/1492 606/41 |
| 6,478,776 B1 * | 11/2002 | Rosenman | ......... | A61B 17/3468 604/164.01 |
| 6,493,591 B1 * | 12/2002 | Stokes | ................... | A61N 1/057 607/127 |
| 6,497,704 B2 * | 12/2002 | Ein-Gal | ............. | A61B 18/1477 606/41 |
| 6,547,787 B1 * | 4/2003 | Altman | ............... | A61B 18/1492 606/41 |
| 6,931,286 B2 * | 8/2005 | Sigg | .................. | A61M 25/0082 607/120 |
| 7,273,478 B2 * | 9/2007 | Appling | ................. | A61B 18/24 606/15 |
| 7,794,444 B2 * | 9/2010 | Lesh | ...................... | A61B 17/22 604/506 |
| 7,945,337 B2 * | 5/2011 | Brabec | ................. | A61N 1/0568 607/122 |
| 8,099,177 B2 * | 1/2012 | Dahlberg | ................. | A61N 1/05 607/127 |
| 8,628,552 B2 * | 1/2014 | Toy | ...................... | A61M 5/3286 606/185 |
| 8,801,665 B2 * | 8/2014 | Sabbah | ............. | A61M 25/0084 604/117 |
| 2001/0012935 A1 * | 8/2001 | Morgan | ............ | A61B 18/1485 606/41 |
| 2002/0082595 A1 * | 6/2002 | Langberg | ........... | A61B 18/1492 606/41 |
| 2005/0055020 A1 * | 3/2005 | Skarda | ................ | A61B 18/1492 606/41 |
| 2005/0240202 A1 * | 10/2005 | Shennib | .................. | A61B 17/08 606/142 |
| 2006/0287700 A1 * | 12/2006 | White | ................... | A61B 5/0215 607/127 |
| 2008/0161804 A1 * | 7/2008 | Rioux | ................ | A61B 18/1477 606/41 |
| 2010/0262232 A1 * | 10/2010 | Annest | ................... | A61F 2/2466 623/2.17 |
| 2010/0280604 A1 * | 11/2010 | Zipory | ............... | A61B 17/0401 623/2.11 |
| 2011/0160533 A1 | 6/2011 | Sampson | | |
| 2011/0213450 A1 * | 9/2011 | Maclean | ................... | A61F 2/95 623/1.11 |
| 2012/0238968 A1 | 9/2012 | Toy et al. | | |
| 2013/0110148 A1 * | 5/2013 | Lalonde | ................ | A61B 18/02 606/185 |
| 2013/0150877 A1 | 6/2013 | Ikeda | | |
| 2013/0165963 A1 * | 6/2013 | Coleman | .......... | A61B 17/12022 606/192 |
| 2013/0211399 A1 * | 8/2013 | Caples | ............... | A61B 18/1492 606/41 |
| 2014/0094787 A1 * | 4/2014 | Reynolds | .......... | A61M 25/0138 606/33 |
| 2014/0277056 A1 | 9/2014 | Poore et al. | | |
| 2018/0153467 A1 * | 6/2018 | Lichtenstein | ........ | A61B 5/6857 |
| 2019/0015205 A1 * | 1/2019 | Rajagopal | ............ | A61F 2/2457 |

OTHER PUBLICATIONS

International Search Report and Written Opinion issued for International Patent Application No. PCT/US2020/058239, dated Feb. 25, 2021, 11 pages.

* cited by examiner

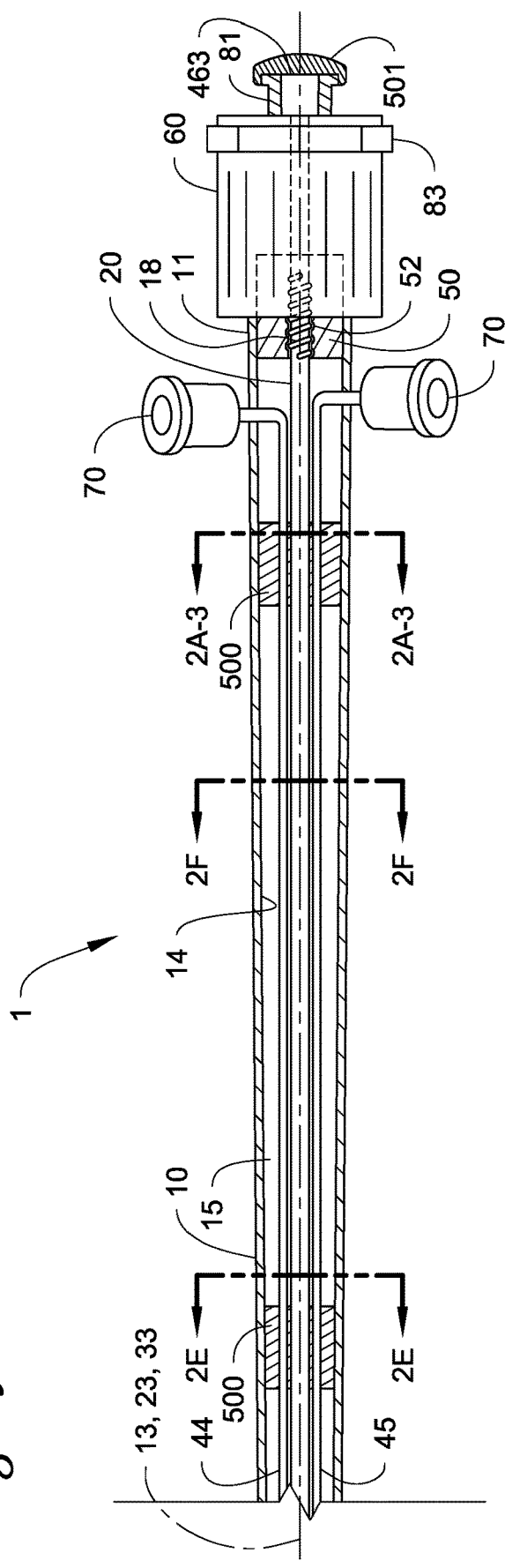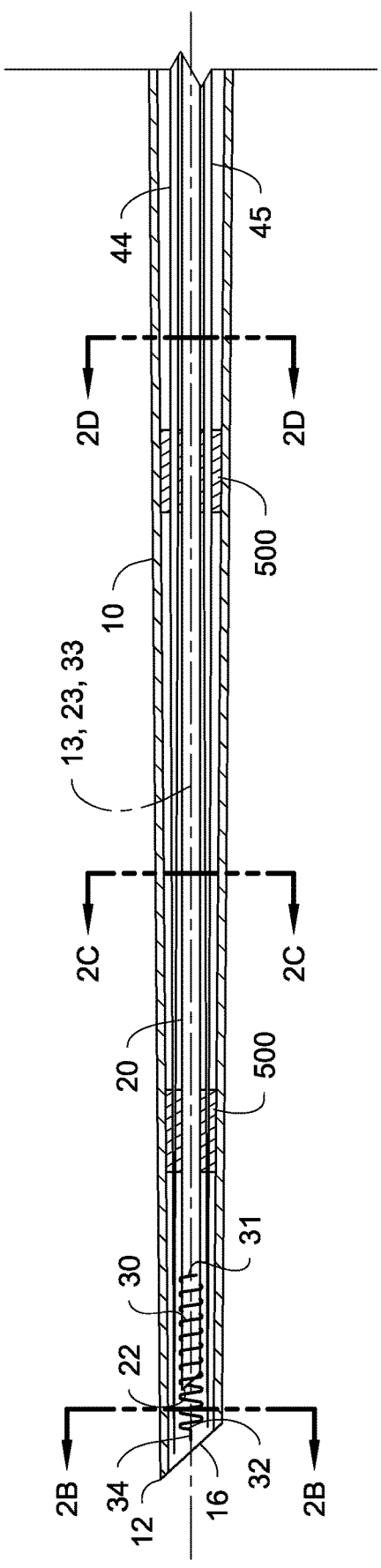

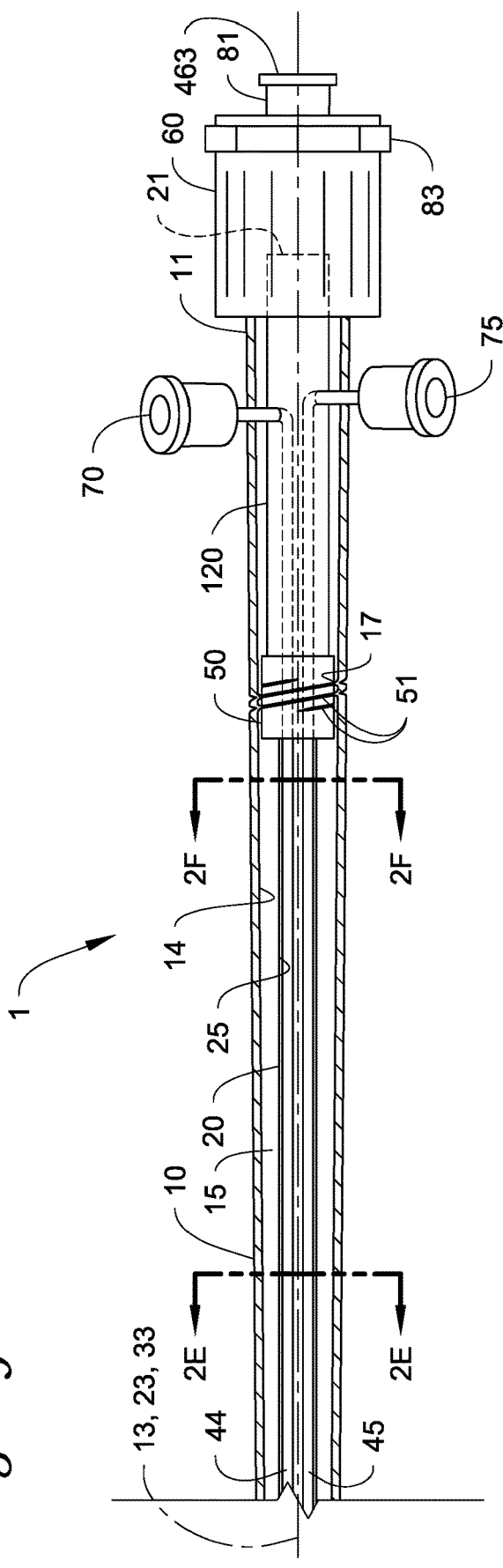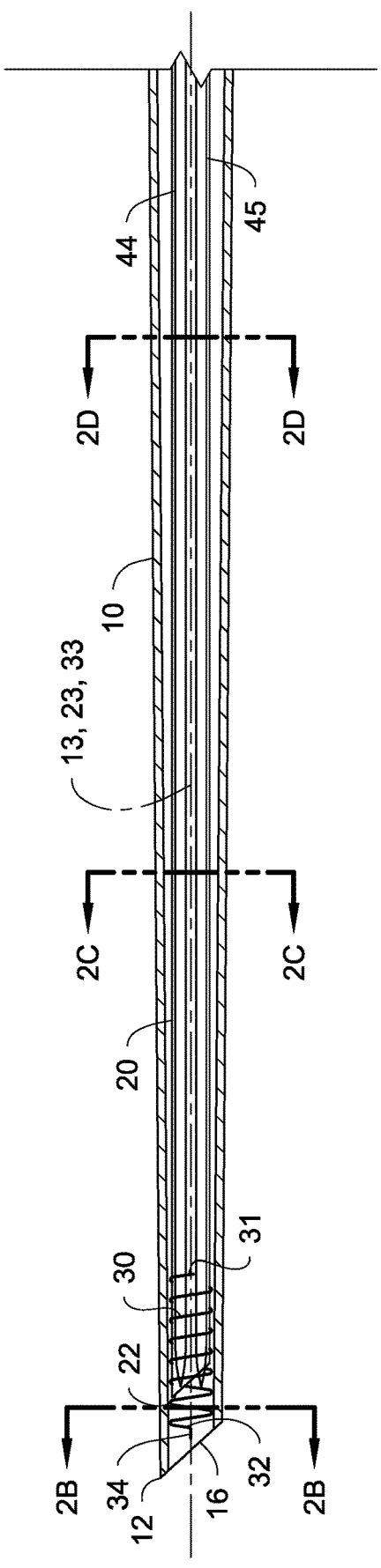

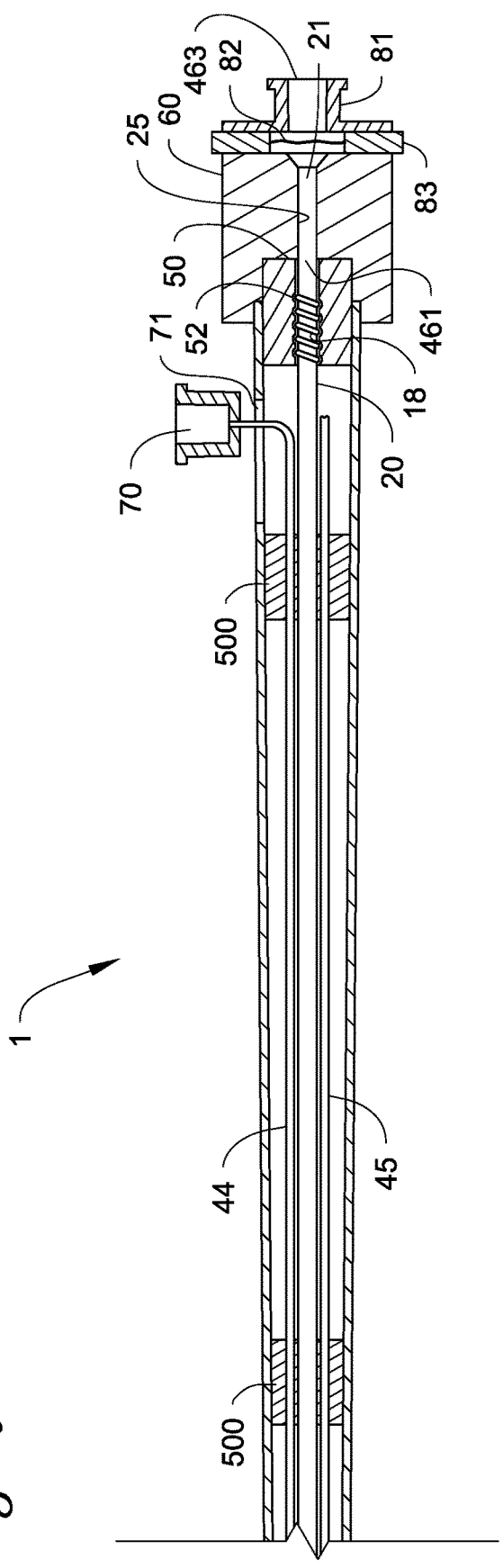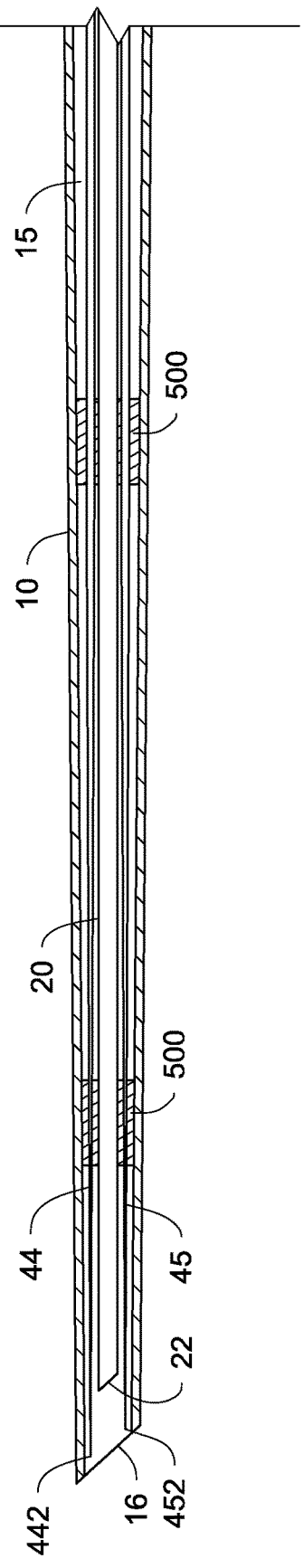

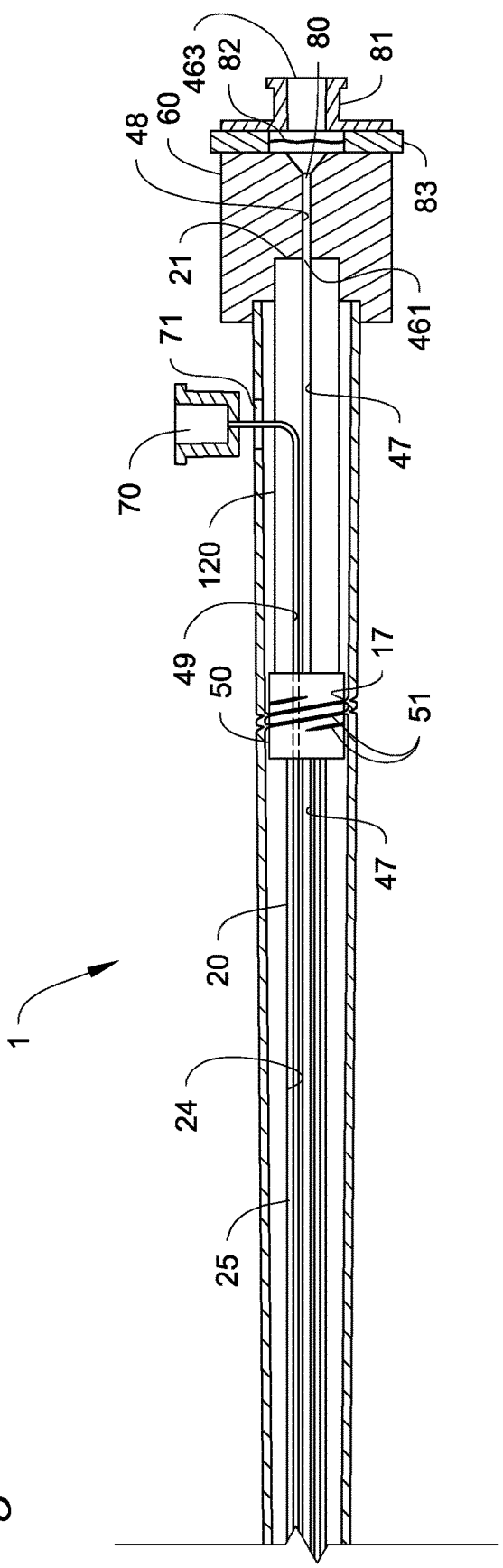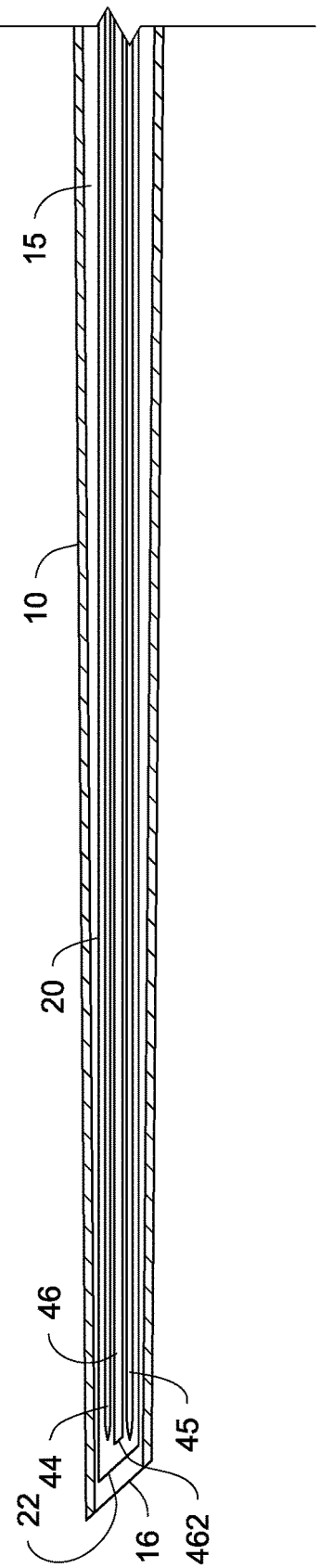

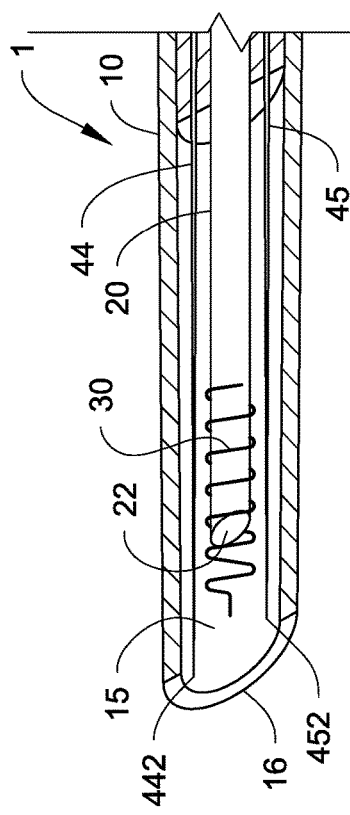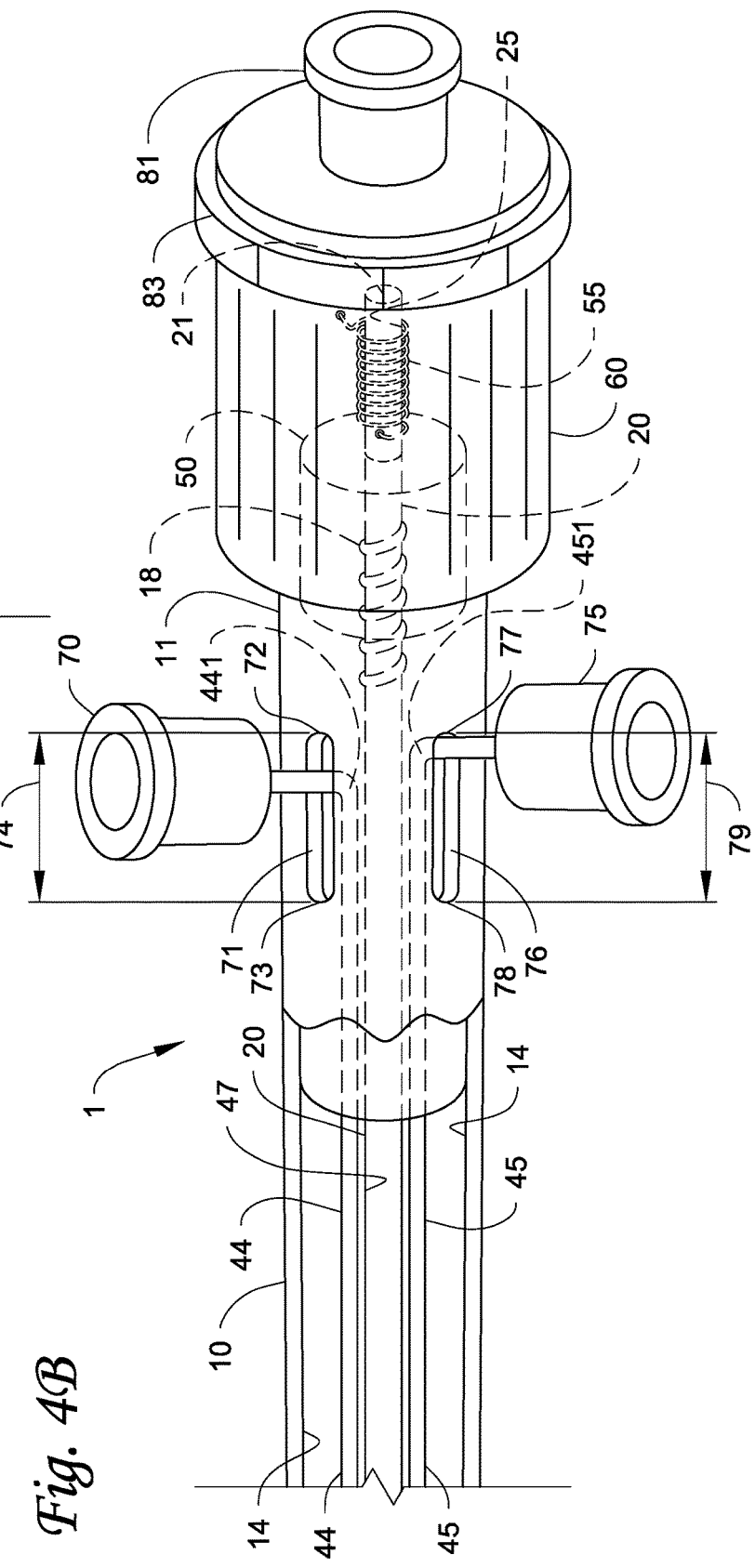
Fig. 4A
Fig. 4B

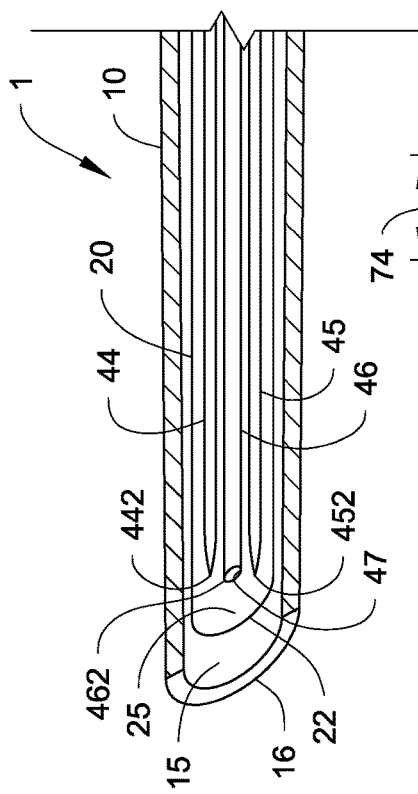
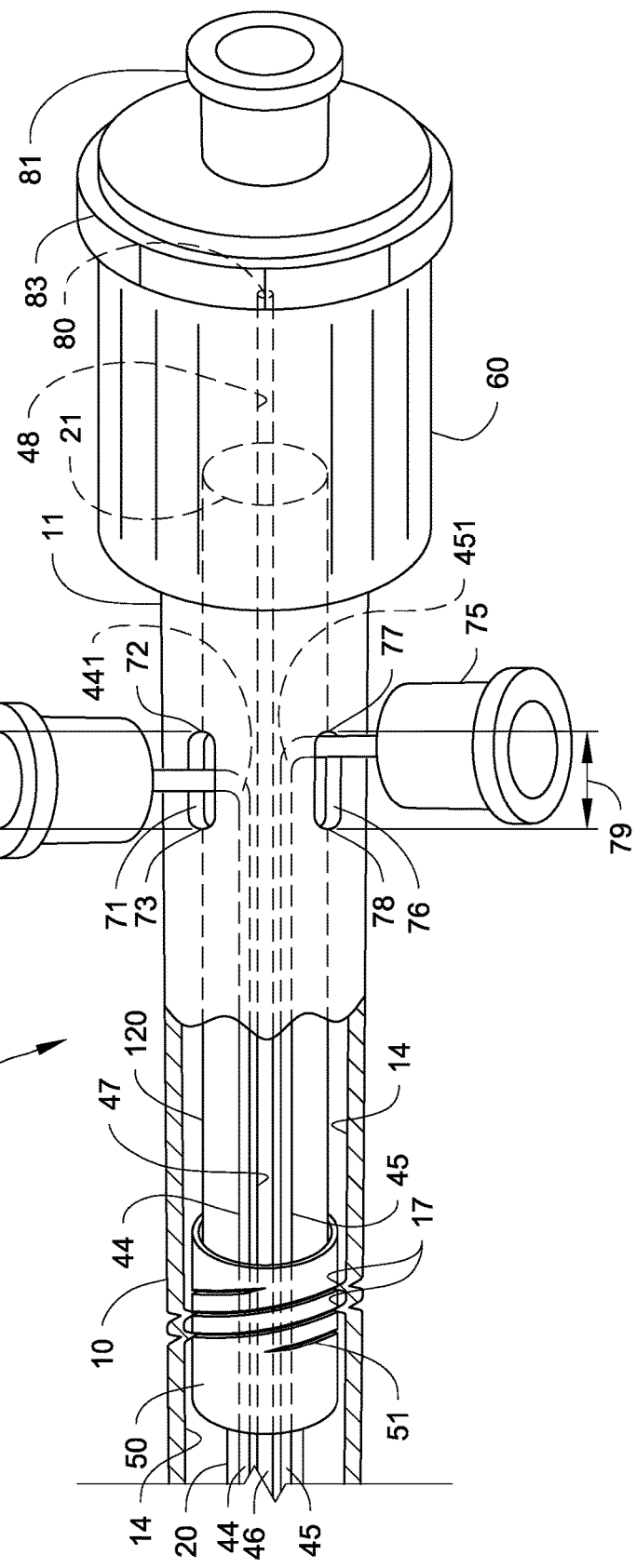
Fig. 5A
Fig. 5B

MEDICAL DEVICE TO ACCESS PERICARDIAL SPACE WITH CONTROL

FIELD

This disclosure is directed to a medical device, operating instructions for its use and also indications and methods for treatment of human patients by delivering therapeutic agents and/or modalities directly to the heart of a patient, or other organs.

BACKGROUND

Despite advancements in medical technologies, myocardial infarction remains the No. 1 cause of death in the world. When a myocardial infarct occurs, the heart tissue is injured and eventually dies due to ischemia caused by complete or incomplete blockage of coronary artery blood flow. This blockage initiates a cascade of events leading to myocardial cell death, apoptosis and necrosis. As the process of cell death continues, the condition can lead to cardiac dysfunction, arrhythmias and potentially cause heart failure, which is a major cause of morbidity in aging humans.

The heart is one of the least regenerative organs. Once heart cells have died, it is extremely unlikely that the lost cells will be replenished with viable and functional myocardial cells. For this reason, morbidity and mortality following an ischemic cardiac injury are both high and are a significant factor in the world-wide cost of healthcare. Effective cardiac regenerative therapies are needed.

To develop methods for cardiac regenerative therapy, delivery of various therapeutic agents and/or modalities to damaged or ischemic heart muscle has been explored. Multiple methods for delivering therapeutic agents to the heart have been tested, including an intravenous injection, delivery by catheter, and direct injection from outside the heart.

Because existing instruments and methods that have been developed to directly inject medication(s) into the heart and pericardial space have had serious attendant risks of complications, including unintentional cardiac wall perforation, hemorrhage, cardiac injury and even patient death, no direct injection techniques are currently in widespread use or have become the standard of care for non-surgical cardiac patients.

SUMMARY

A medical device that allows accurate, timely, and safe direct delivery of agents and/or modalities into an organ of a patient is described. This medical device can mitigate the risk of unintended puncture of the organ wall caused by the inability to precisely control the insertion depth of the delivery mechanism. The medical device also allows simultaneous or sequential delivery of agents and/or modalities to the same area of the organ.

Problems to be Solved

The problem to be solved is described taking the heart of a patient suffering from a cardiac condition as an example. However, the similar precise insertion depth control of a delivery mechanism is also needed for organs other than the heart. The disclosure should be easily modified to be adapted for use for organs other than the heart.

Previous techniques of direct delivery to the heart had a risk of unintended puncturing of the heart wall and penetrating into the lumen of the heart. In particular, in patients suffering from ischemic heart disease, the thickness of the heart wall is often reduced, and such patients have higher risk of getting unintended puncturing of the heart wall. Such unintended puncturing can cause hemorrhage from the heart and cardiac tamponade, and presents a significant risk factor in performing the direct delivery procedure. Unintended punctures are caused because these needles lacked means for controlling the insertion depth. A device and a method that provide safe direct delivery of agents and/or modalities into the heart were needed.

Furthermore, when a simultaneous or sequential delivery of more than one agents and/or modalities to the same area of the heart was desired, it was difficult to target the first-targeted area with the second delivery device, because the first delivery device had to be removed from the heart to use the second delivery device. A device and methods that can assist the simultaneous or sequential delivery of more than one agents and/or modalities to the same area of the heart without having to remove the first device was desired.

The object of the present disclosure can provide solutions to the above-described problems. Disclosed is a device that has an insertion depth control mechanism that can assist delivery of agents and/or modalities into the heart and can deliver a plurality of agents and/or modalities into the same area of the heart. A method for treating cardiac conditions by simultaneously or sequentially delivering agents and/or modalities to the heart is also disclosed.

Means for Solving the Problem

Embodiments disclosed in the present disclosure can solve the above-described problems and relate to a medical device. The medical device has an outer tubular body and an inner tubular body, which move relative to each other in a predetermined direction and distance. A tissue engagement member is attached to the distal end of the inner tubular body, and the tissue engagement member and the inner tubular body form a unit. The tissue engagement member has a helical shape. The helical tissue engagement member and the inner tubular body unit is retractable inside the outer tubular body. The advancement and retraction of the helical tissue engagement member and the inner tubular body is guided by a helical groove cut in a gear that guides a corkscrew-like movement of the inner tubular body. Rotation of the inner tubular body relative to the outer tubular body in one direction advances the inner tubular body so that a portion of the attached helical tissue engagement member is exposed from the distal end of the outer tubular body. Rotation of the inner tubular body to the second direction retracts the inner tubular body and the attached helical tissue engagement member into the outer tubular body. As the tissue engagement member is exposed outside of the outer tubular body by a corkscrew-like movement, the tip of the tissue engagement member can penetrate the pericardium and the tissue engagement member can secure inside the pericardium or in the myocardium by the corkscrew-like movement. The corkscrew-like movement of the tissue engagement member is limited to a predetermined angle, and thus, advancement of the inner tubular body is limited to a predetermined distance. By this configuration, the risk of an unintended puncture of the heart wall can be reduced. As the tissue engagement member can secure the medical device onto the heart and prevent the movement of the medical device during application, multiple agents and/or modalities can be applied through the inner tubular body either simultaneously or sequentially to the targeted area of the heart. The agents and/or modalities can be supplied through one or more delivery mechanism placed inside of the outer tubular body.

Effects of the Disclosure

The medical device of the present disclosure can be used to deliver agents and/or modalities directly into the heart while mitigating the risk of an unintended puncture of the heart wall. In addition, the medical device can allow simultaneous or sequential application of agents and/or modalities to the same area of the heart. The medical device can easily be adapted to be used to for direct delivery of agents and/or modalities to organs other than the heart.

While multiple embodiments are disclosed, still other embodiments of the present disclosure will become apparent to those skilled in the art from the following detailed description. As will be realized, the disclosure can be modified in various aspects, all without departing from the spirit and scope of the present disclosure. Accordingly, the drawings and detailed description are to be regarded as illustrative in nature and not restrictive.

A medical device for delivering an agent and/or a modality to an organ is disclosed. The medical device has an outer tubular body having a first proximal end, a first distal end, a first lumen extending between the first proximal end and the first distal end, and a first longitudinal axis extending from the first proximal end to the first distal end. The inner tubular body has a second proximal end, a second distal end, a second lumen extending between the second proximal end and the second distal end, and a second longitudinal axis extending from the second proximal end to the second distal end. The inner tubular body is moveable in the first lumen of the outer tubular body. The second proximal end of the inner tubular body is operably coupled to the first proximal end of the outer tubular body, and the inner tubular body is moveable along the first longitudinal axis of the outer tubular body from a first position to a second position. A helical tissue engagement member has a third proximal end, a third distal end, and a third longitudinal axis extending from the third proximal end to the third distal end. The helical tissue engagement member is attached to the second distal end of the inner tubular body, and the third longitudinal axis of the helical tissue engagement member is substantially parallel to the first longitudinal axis of the outer tubular body and the second longitudinal axis of the inner tubular body. The helical tissue engagement member is located in the first lumen of the outer tubular body. The third distal end of the helical tissue engagement member is recessed relative to the first distal end of the outer tubular body when the inner tubular body is at the first position, and the third distal end of the helical tissue engagement member extends out of the first distal end of the outer tubular body when the inner tubular body is at the second position.

A method for treating or monitoring a patient suffering from a cardiac condition is disclosed. The method includes delivering one or more agents and/or modalities directly to a cardiac muscle of a patient in need thereof.

BRIEF DESCRIPTION OF THE DRAWINGS

Figures are not drawn to scale and are for illustrative purpose only. Dimensions, such as relative size and thickness can be adjusted for specific applications.

FIG. 2A-1 and FIG. 2A-2 are side views of the medical device according to one embodiment. Portions of outer tubular body and inner tubular body are removed. FIG. 2A-1 shows the proximal half and FIG. 2A-2 shows the distal half of the medical device. FIG. 2A-3 and FIGS. 2B-2F show cross sections of the medical device at positions indicated in FIGS. 2A-1 and 2A-2. In FIGS. 2B-2F, only the outer tubular body is shown. FIG. 2G-1 and FIG. 2G-2 are side views of the medical device according to another embodiment. Portions of outer tubular body and inner tubular body are removed.

FIG. 3A and FIG. 3B are cross-sections along the long axis of the medical device according to one embodiment. FIG. 3C and FIG. 3D are cross-sections along the long axis of the medical device according to another embodiment.

FIG. 4A is an enlarged cross-section of the side-distal isometric view of the distal end of the medical device according to one embodiment with two needles. FIG. 4B is an enlarged side-proximal isometric view of the proximal end of the medical device according to one embodiment.

FIG. 5A is an enlarged cross-section of the side-distal isometric view of the distal end of the medical device according to one embodiment with two needles. FIG. 5B is an enlarged side-proximal isometric view of the proximal end of the medical device according to one embodiment.

LEGENDS TO THE FIGURE

Figure 1A:
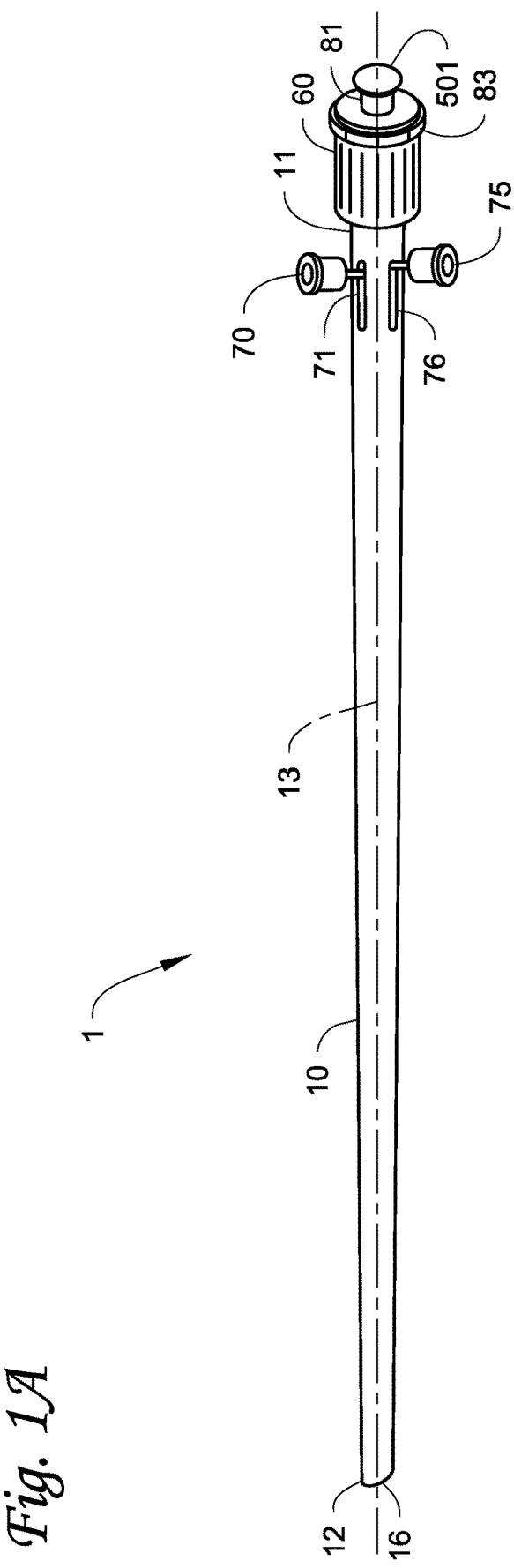
FIG. 1A is a side-proximal isometric view of the medical device according to one embodiment.

Like reference numbers represent like parts throughout.
1: medical device
10: outer tubular body
11: first proximal end of the outer tubular body
12: first distal end of the outer tubular body
13: first longitudinal axis of the outer tubular body
14: first inner surface of the outer tubular body
15: first lumen of the outer tubular body
16: cutting edge
17: protrusions formed on outer tubular body
18: protrusions formed on inner tubular body
20: inner tubular body
21: second proximal end of the inner tubular body
22: second distal end of the inner tubular body
23: second longitudinal axis of the inner tubular body
24: second inner surface of the inner tubular body
25: second lumen of the inner tubular body 30: tissue engagement member
31: third proximal end of the tissue engagement member
32: third distal end of the tissue engagement member
33: third longitudinal axis of the tissue engagement member
34: tip
44: needle 1
45: needle 2
46: center tubular body
47: lumen of the center tubular body
50: gear
51, 52: helical groove
60, 160: thumb button
70: sideport 1
71: slit 1
72: proximal end of slit 1
73: distal end of slit 1
74: travel distance of sideport 2
75: sideport 2
76: slit 2
77: proximal end of slit 2
78: distal end of slit 2
79: travel distance of sideport 2
80: center tubing
81: center luer lock
82: valve
83, 183: ring to control valve
84: holder
85: device-receiving part of the holder
86: thread
87: protrusion
88: handle
89: trigger
90: heart
91: pericardium
92: pericardial space
93: myocardium
100: subject
101: body wall
120: widened part of the inner tubular body
441: proximal end of needle 1
442: distal end of needle 1
451: proximal end of needle 2
452: distal end of needle 2
461: proximal end of center tubular body
462: distal end of center tubular body
463: proximal end of the medical device
500: needle guide
501: cap

DETAILED DESCRIPTION OF THE DISCLOSURE

A "heart" refers generally to all parts of the heart and includes pericardium, myocardium, pericardial space, ventricle, atrium, septum, coronary artery, and atrium.

A "heart muscle" refers generally to myocardium.

A "same area" of the heart refers to substantially overlapping areas that applied agents and/or modalities can have effect on, but is not limited to identical areas.

"Delivering" to the heart includes injection or superficial application of agents and/or modalities to the heart. Application of modalities includes application of electric current or voltage via an electrode, and measurement of current or voltage via an electrode.

Forming a "tight seal" means that, when two items are connected, no or negligible air or liquid leaks in or out of the connection when a medically appropriate pressure is applied.

"Puncture/puncturing," "unintended puncture/puncturing," "penetrate/penetrating," and "unintentionally penetrate/penetrating" of the heart means complete penetration of the heart wall by an object, which can cause leaking of blood from the heart.

This disclosure relates generally to a medical device and methods for treating patients and for operating the medical device. More specifically, the present disclosure relates to a device, and methods, for delivering agents and/or modalities directly to an organ of a patient while mitigating the risk of an unintended puncture of the organ wall. The following embodiment is described using the heart of a patient as an example; however, the medical device can also be applied for direct delivery of agents and/or modalities into organs other than the heart.

Embodiments

Figure 1B:
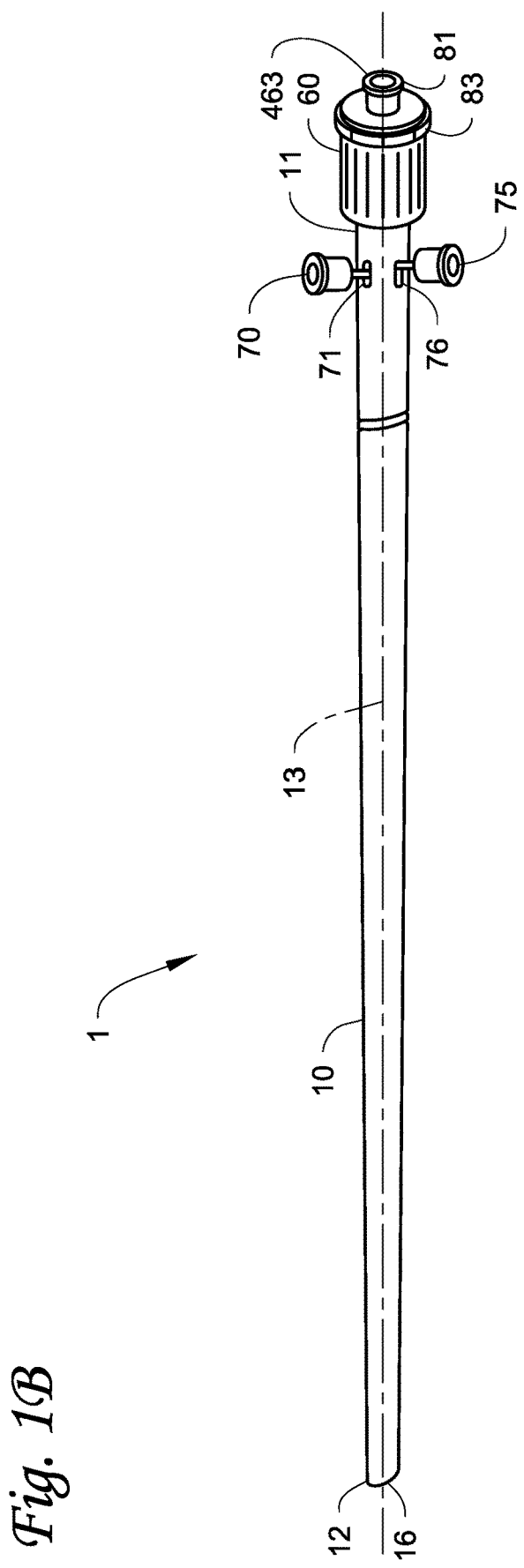
FIG. 1B is a side-proximal isometric view of the medical device according to another embodiment.

FIGS. 1A and 1B are side-proximal isometric views of the medical device according to some embodiments. The medical device (1) has an outer tubular body (10) and a thumb button (60). The outer tubular body (10) has a first proximal end (11) and a first distal end (12). A first longitudinal axis (13) extends in the direction from the first proximal end (11) to the first distal end (12). On the side of the outer tubular body (10) close to the first proximal end (11), sideport 1 (70) and sideport 2 (75) are movably disposed via slit 1 (71) and slit 2 (76), respectively. Sideport 1 (70) and sideport 2 (75) are staggered at an angle around a circumferential profile of the sidewall of the outer tubular body (10). The angle at which sideport 1 (70) and sideport 2 (75) are disposed can be 0-180°. The thumb button (60) can have a ring (83) to control a valve (not shown) that is independently movable from the thumb button (60) and rotates around the first longitudinal axis (13). The thumb button (60) can have a center luer lock (81) at the proximal end (463) of the medical device (1). The center luer lock (81) can be optionally fitted with a cap (501). The operation of the sideport 1 (70), the sideport 2 (75), the thumb button (60), the ring to control the valve (83), and the center luer lock (81) are described in detail later in this specification. Inside the outer tubular body (10), an inner tubular body is disposed, which is not shown in this figure and will be described later in this specification.

Figure 2B:
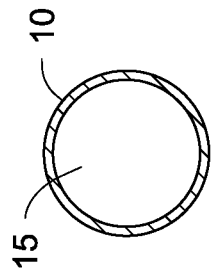
Figure 2C:
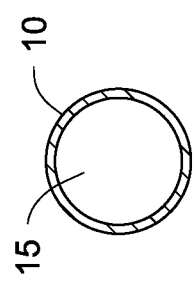
Figures 2, 2A, 3:
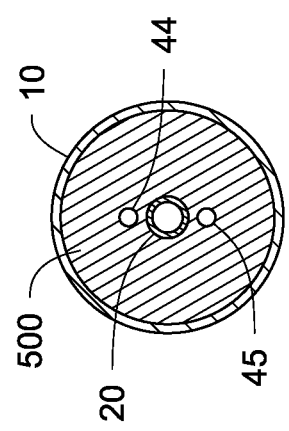
Figure 2D:
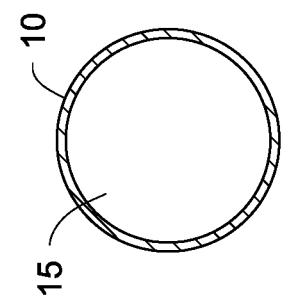
Figure 2E:
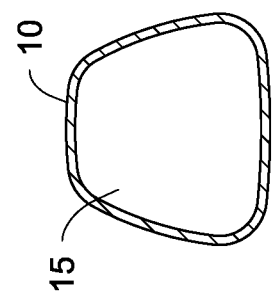
Figure 2F:
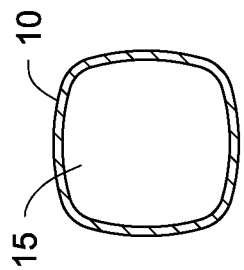

FIG. 2A-1 and FIG. 2A-2 are side views of the medical device (1) according to one embodiment. An example with two needles is shown. FIG. 2A-1 is a proximal part of the medical device (1) and FIG. 2A-2 is a distal part of the medical device (1). Portions of the outer tubular body (10) and inner tubular body (20) are removed to show inside. FIGS. 2A-3, 2B-2F are cross sections at the positions indicated in FIGS. 2A-1 and 2A-2. In FIGS. 2B-2F, only the outer tubular body (10) is shown.

The medical device (1) has an inner tubular body (20), and a helical tissue engagement member (30) inside of the outer tubular body (10). The outer tubular body (10) has a first inner surface (14) and a first lumen (15) extending in the direction of the first longitudinal axis (13)

The outer tubular body (10) of the medical device (1) can be made of stainless steel or any surgically suitable material. The outer surface of the outer tubular body (10) can be tapered such that the outer diameter of the outer tubular body (10) increases from the first distal end (12) towards the first proximal end (11). The first distal end (12) of the outer tubular body (10) can be beveled, and can have a cutting edge (16) so as to assist with penetrating the body wall (101) (see FIGS. 7A and 7B) of the subject (100) (see FIG. 6). The outer tubular body (10) can be shaped so as to make the insertion into the patient easy and to prevent bending of the medical device (1) due to the pressure from the body. For example, the shapes of cross sections of the outer tubular body (10) can be circular at portions close to the proximal and distal ends, and can gradually change to a rounded square-like and rounded trapezoid shapes at middle portions. An example of a series of cross sections is presented in FIGS. 2B-2F, but the outer tubular body (10) can be configured in any shapes in any orders that make the insertion into the patient easy and prevent bending due to the pressure from the body.

The inner tubular body (20) has a second proximal end (21, see FIG. 3A), a second distal end (22), a second longitudinal axis (23) extending between the second proximal end (21) and the second distal end (22), and a second lumen (25), extending in the direction of the second longitudinal axis (23). The inner tubular body is connected to a gear (50) and can have a widened part (120) on its proximal side.

The inner tubular body (20) is movably disposed in the first lumen (15) of the outer tubular body (10). The inner tubular body (20) is operably coupled to the first proximal end (11) of the outer tubular body (10) and a thumb button (60). The inner tubular body (20) is displaceable along the first longitudinal axis (13) of the outer tubular body (10) from a first position to a second position. The movement of the inner tubular body (20) can be corkscrew-like, rotating around the second longitudinal axis (23) as it moves between the first position and the second position.

The gear (50) attached to the outer tubular body (10) has a helical groove (52), which is configured to engage with protrusions (18) formed on the the inner tubular body (20). The helical groove (52) and the protrusions (18) are configured to guide a corkscrew-like movement of the inner tubular body (20). The helical groove (52) is formed so that the rotation of the inner tubular body (20) is limited to a predetermined angle.

The rotation of the inner tubular body (20) can be guided by the gear (50) so that when the inner tubular body (20) is rotated in a first direction around the second longitudinal axis (23), the inner tubular body (20) and the helical tissue engagement member (30) move towards the first distal end (12) of the outer tubular body (10), and when the inner tubular body (20) is rotated in a second direction around the second longitudinal axis (23), the inner tubular body (20) and the helical tissue engagement member (30) move towards the first proximal end (11) of the outer tubular body (10).

The thumb button (60) is configured to trigger the movement of the inner tubular body (20). The mechanism for rotating the inner tubular body (20) is not particularly limited, and can be any one of suitable rotation-control mechanisms, including manual rotation, a spring (55)-operated mechanism, a torsional hub, and an electromechanically controlled device.

The medical device (1) can be configured so that the rotatable range of the inner tubular body (20) relative to the outer tubular body (10) is limited to a first predetermined angle, and each operation of the thumb button (60) allows a rotation of the inner tubular body (20) relative to the outer tubular body (10) by a second predetermined angle.

The helical tissue engagement member (30) has a third proximal end (31), a third distal end (32), and a third longitudinal axis (33) extending from the third proximal end (31) to the third distal end (32). The third proximal end (31) of the helical tissue engagement member (30) is attached to the inner tubular body (20), on the second distal end (22) side, and further extends towards the distal direction of the inner tubular body (20). The first longitudinal axis (13) of the outer tubular body (10), the second longitudinal axis (23) of the inner tubular body (20), and the third longitudinal axis (33) of the helical tissue engagement member (30) are substantially parallel to each other or substantially overlap.

The helical tissue engagement member (30) moves together with the inner tubular body (20) as a unit. In operation, the third distal end (32) of the helical tissue engagement member (30) is recessed relative to the first distal end (12) of the outer tubular body (10) when the inner tubular body (20) is at the first position, and the third distal end (32) of the helical tissue engagement member (30) extends out of the first distal end (12) of the outer tubular body (10) when the inner tubular body (20) is at the second position.

The tissue engagement member (30) can have a tip (34) at the third distal end (32). In operation, when the inner tubular body (20) is moved from the first position to the second position, the tip (34) can make a cut in the pericardium (91) or penetrate through the pericardium (91) (see FIGS. 7A-8B; this feature will be described in detail later in this specification). By the corkscrew-like movement, the tissue engagement member (30) can be engaged with the pericardium (91) or myocardium (93) (see FIGS. 7A-8B). The free end of the tip (34) can be blunt so as not to cause unintended damage to the subject's heart (90) (see FIG. 6).

The medical device (1) can further include at least one delivery mechanism. The delivery mechanism is located in the first lumen (15) of the outer tubular body (10), and is operably coupled to the outer tubular body (10). In FIGS. 2A-1 and 2A-2, an example with two needles, needle 1 (44) and needle 2 (45), are shown. Needle 1 (44) is connected to sideport 1 (70), and needle 2 (45) is connected to sideport 2 (75). The movement of the needles is guided by needle guides (500). The at least one delivery mechanism will be described further below.

FIGS. 2G-1 and 2G-2 show the medical device (1) in another embodiment. In this embodiment, the gear (50) attached to the inner tubular body (20) has a helical groove (51), which is configured to engage with protrusions (17) formed on the first inner surface (14) of the outer tubular body (10) towards the first lumen (15) of the outer tubular body (10). The helical groove (51) and the protrusions (17) are configured to guide a corkscrew-like movement of the inner tubular body (20). The helical groove (51) is formed so that the rotation of the gear (50) and the inner tubular body (20) is limited to a predetermined angle.

FIG. 3A and FIG. 3B are cross-sections along the long axis of the medical device (1) according to one embodiment. FIG. 3A shows a proximal part of the medical device (1) and FIG. 3B shows a distal part of the medical device (1). An example with two needles is shown. Tissue engagement member is not shown.

The medical device (1) can comprise at least one delivery mechanism. The delivery mechanism is located in the first lumen (15) of the outer tubular body (10), and is operably coupled to the outer tubular body (10). The delivery mechanism is displaceable along the first longitudinal axis (13) of the outer tubular body (10) from a third position (a retracted position) to a fourth position (an exposed position). In operation, the distal end of the delivery mechanism is recessed relative to the first distal end (12) of the outer tubular body (10) when the delivery mechanism is at the third position, and extends out of the second distal end (12) of the outer tubular body (10) when the delivery mechanism is at the fourth position.

In FIGS. 3A and 3B, the delivery mechanism is explained using an example with two needles. However, the delivery mechanism is not limited to these examples, and can be switched with other embodiments, for example, a catheter, a guide-wire, electrodes, leads, and a camera. The delivery mechanisms can be configured to be exclusively used or used at the same time.

In the examples shown in FIG. 3A and FIG. 3B, the lumen of the needle 1 (49) is continuous with the sideport 1 (70) and opens into the bottom of the sideport 1 (70). The lumen of the needle 2 is continuous with the sideport 2 (not shown) and opens into the bottom of the sideport 2 (not shown).

The inner tubular body (20) is disposed in the first lumen of outer tubular body (15). The proximal end of the inner tubular body (21) opens towards the proximal end (463) of the medical device (1). At the proximal end of the medical device (463), a center luer lock (81) may be disposed. The center luer lock (81) is configured to receive a tubing, a stopcock, other medical devices or the like and is configured to form a tight seal. The center luer lock (81) may be configured to receive a cap (501). The cap can be in any shape or material that prevents contamination of the center luer lock (81) when the center luer lock (81) is not being used.

A valve (82) and a ring (83) to control valve can be disposed on the thumb button (60). The opening of the valve (82) can change from completely closed to completely open and the ring to control valve (83) is configured to control the opening size of the valve (82). The center luer lock (81) or a structure that performs a similar function can be placed distal or proximal to the valve (82). The center luer lock (81) or a structure that performs a similar function can be enclosed inside of the thumb button (60) or can be exposed as shown in FIGS. 1A-2A-1, 2G-1, 3A, 3C, 4B, and 5B. The shape of the thumb button (60) is not limited to the shape shown in FIGS. 1A-6, and can be any ergonomically suitable shape as shown, for example, in the embodiment of FIG. 10 (see thumb button (160) and ring (183) to control valve). The mechanism to control the valve (82) can be in many shapes including a ring, a lever, or a button.

In operation, the valve (82) provides control of the flow of material provided through the inner tubular body (20). Alternatively, an external tube can be inserted through the opening of the valve (82) and connected to the inner tubular body (20) distally to the valve (82). In the latter case, the valve (82) provides a barrier for maintaining the sterility of the connection.

Another embodiment is shown as cross sections along the long axis of the medical device (1) in FIGS. 3C and 3D. FIG. 3C shows a proximal part of the medical device (1) and FIG. 3D shows a distal part of the medical device (1). An example with optional two needles (44 and 45) and an optional center tubular body (46) as delivery mechanisms is shown. Tissue engagement member is not shown. A center tubular body (46) is disposed in the second lumen (25) of inner tubular body (20). The center tubular body (46) has a proximal end (461) and a distal end (462) and has a hollow structure. The proximal end of the center tubular body (461) can be continuous with a center tubing (80). The lumen of the center tubular body (47) is continuous with the lumen of the center tubing (48) and opens towards the proximal end (463) of the medical device (1).

FIG. 4A is an enlarged cross-section of the side-distal isometric view of the distal end of the medical device (1) and FIG. 4B is an enlarged side-proximal isometric view of the proximal end of the medical device (1) according to one embodiment. Two needles (needle 1 (44) and needle 2 (45)) and the inner tubular body (20) are shown. Parts of the outer tubular body (10) and the inner tubular body (20) are removed to show the inside. The tissue engagement member is not shown. Needles are at the third (retracted) position, being recessed relative to the first distal end of the outer tubular body (12). The second distal end (22) of the inner tubular body (20) may be blunt or beveled.

The delivery mechanism can be configured to move between the third position (a retracted position) and the fourth position (an exposed position) by moving the sideport. In an example shown in FIGS. 4A and 4B, in which the delivery mechanisms are needles, a needle 1 (44) is connected to a sideport 1 (70) and a needle 2 (45) is connected to a sideport 2 (75). The needle 1 (44) and the needle 2 (45) are separately movable by operating the sideport 1 (70) and the sideport 2 (75), respectively. The moving distances, (74) and (79), of the needle 1 (44) and the needle 2 (45), are limited by a slit 1 (71) and a slit 2 (76) formed on the side of the outer tubular body (10), respectively. When the sideport 1 (70) is at the proximal end of the slit 1 (72), the needle 1 (44) is at the third position (the retracted position), and when the sideport 1 (70) is at the distal end of slit 1 (73), the needle 1 (44) is at the fourth position (the exposed position). Likewise, when the sideport 2 (75) is at the proximal end of the slit 2 (77), the needle 2 (45) is at the third position (the retracted position), and when the sideport 2 (75) is at the distal end of slit 2 (78), the needle 2 (45) is at the fourth position (the exposed position).

In operation, therapeutic agents and/or modalities can be supplied through the sideport 1 (70) and the sideport 2 (75) into the proximal end (441) of the needle 1 (44) and the proximal end (451) of needle 2 (45) and delivered from the distal end (442) of the needle 1 (44) and distal end (452) of the needle 2 (45), respectively.

Sideport 1 (70) and sideport 2 (75) can be configured so as to connect with a tubing, a stopcock, a syringe, or other medical devices. The stopcock can be configured to prevent air or fluid leakage, and to fluidly connect a syringe, a tube, or other medical devices to the medical device (1).

FIG. 5A is an enlarged cross-section of the side-distal isometric view of the distal end and FIG. 5B is an enlarged side-proximal isometric view of the proximal end of the medical device (1) according to another embodiment. Optional two needles (needle 1 (44) and needle 2 (45)) and a center tubular body (46) are shown. Parts of the outer tubular body (10) and the inner tubular body (20) are removed to show the inside. The tissue engagement member is not shown.

The medical device (1) can optionally include a center tubular body (46). The center tubular body (46) is another embodiment of a delivery mechanism and has a lumen (47). The second distal end of the inner tubular body (22) can be blunt or beveled. The distal end of the center tubular body (462) can also be blunt or beveled. The lumen of the center tubular body (47) is continuous with a center tubing (80) at the proximal end of the center tubular body, which opens to the proximal end (463) of the medical device (1). The proximal end (461) of the center tubular body (46) is operatively connected to the thumb button (60) so that the center tubular body (46) moves together with the inner tubular body (20) when the thumb button (60) is operated.

The center tubular body (46) can be wider than the needle 1 (44) and the needle 2 (45), and fluids can pass in both directions of the center tubular body (46). In operation, for example, the center tubular body (46) can aspirate fluid or materials present in the tissue. Alternatively, the center tubular body (46) can "wash" the tissue, for example, by first delivering saline to the tissue and next removing the injected saline. Furthermore, the center tubular body (46) can deliver materials with higher viscosity, such as a gel.

In operation, the agents and/or modalities delivered using the medical device (1) include medicament, growth factors, cells, electrical current, voltage, and an electric signal.

Figure 6:
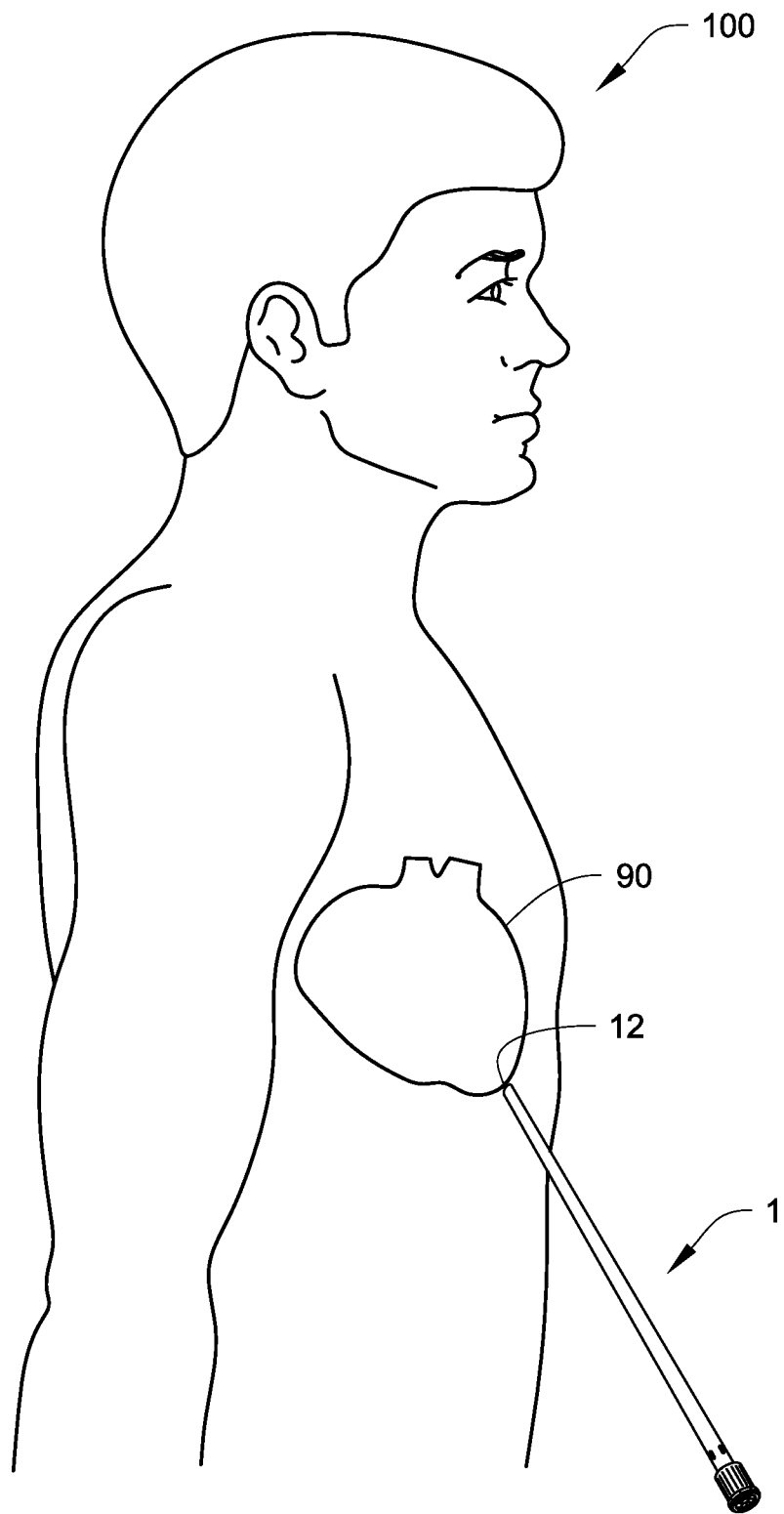
FIG. 6 is a diagram according to one embodiment showing the medical device inserted into a patient to treat the heart.

FIG. 6 is a diagram according to one embodiment showing the medical device (1) inserted into a patient to treat the heart (90). During the insertion of the medical device (1) into the subject (100), the inner tubular body (not shown) is kept at the first position, and the tissue engagement member (not shown) and the delivery mechanisms (not shown) are retracted inside the medical device (1).

Figure 7A:
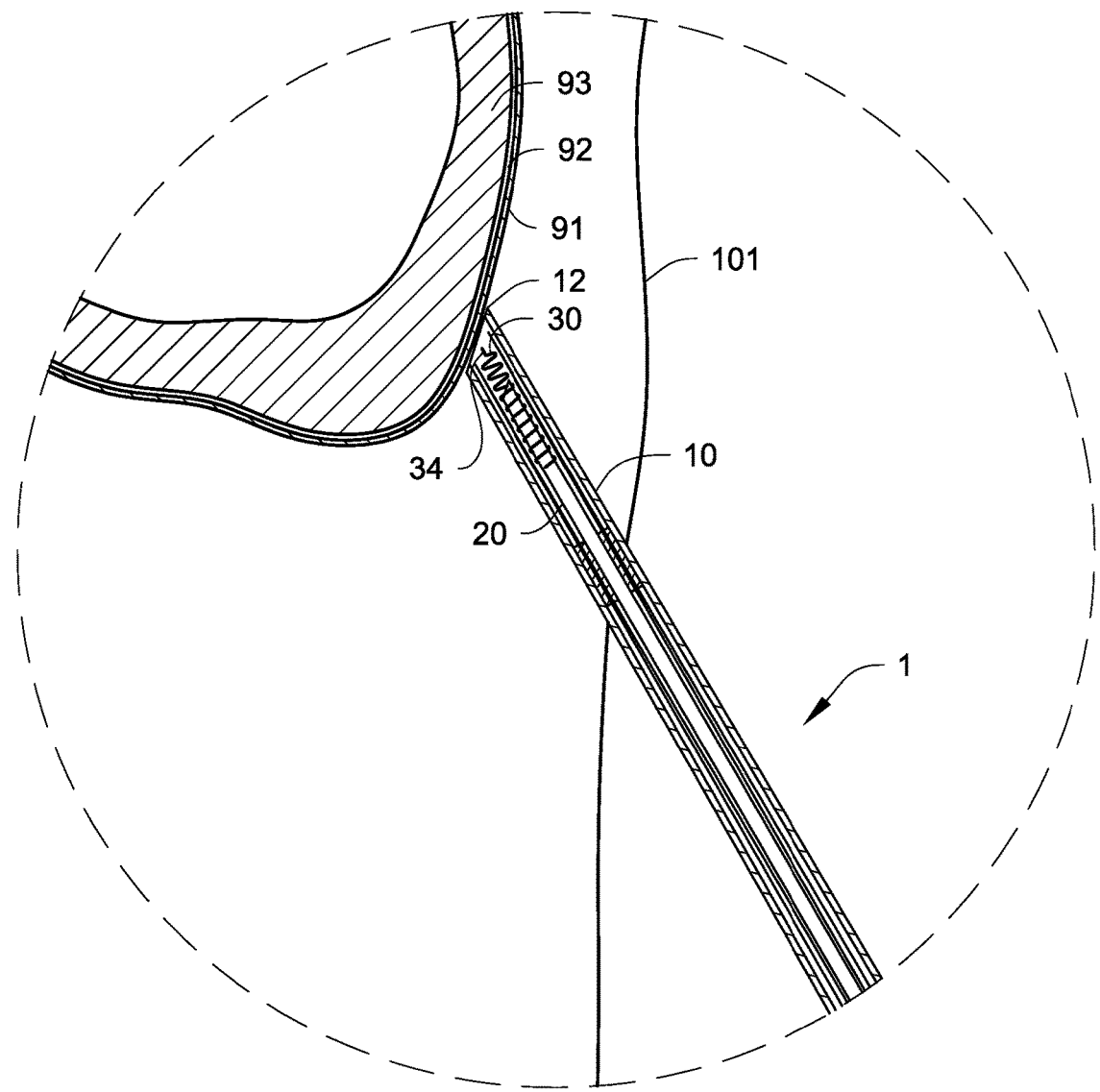
FIG. 7A is a diagram according to one embodiment showing the distal end of the medical device inserted into the body cavity and touching the pericardium.
Figure 7B:
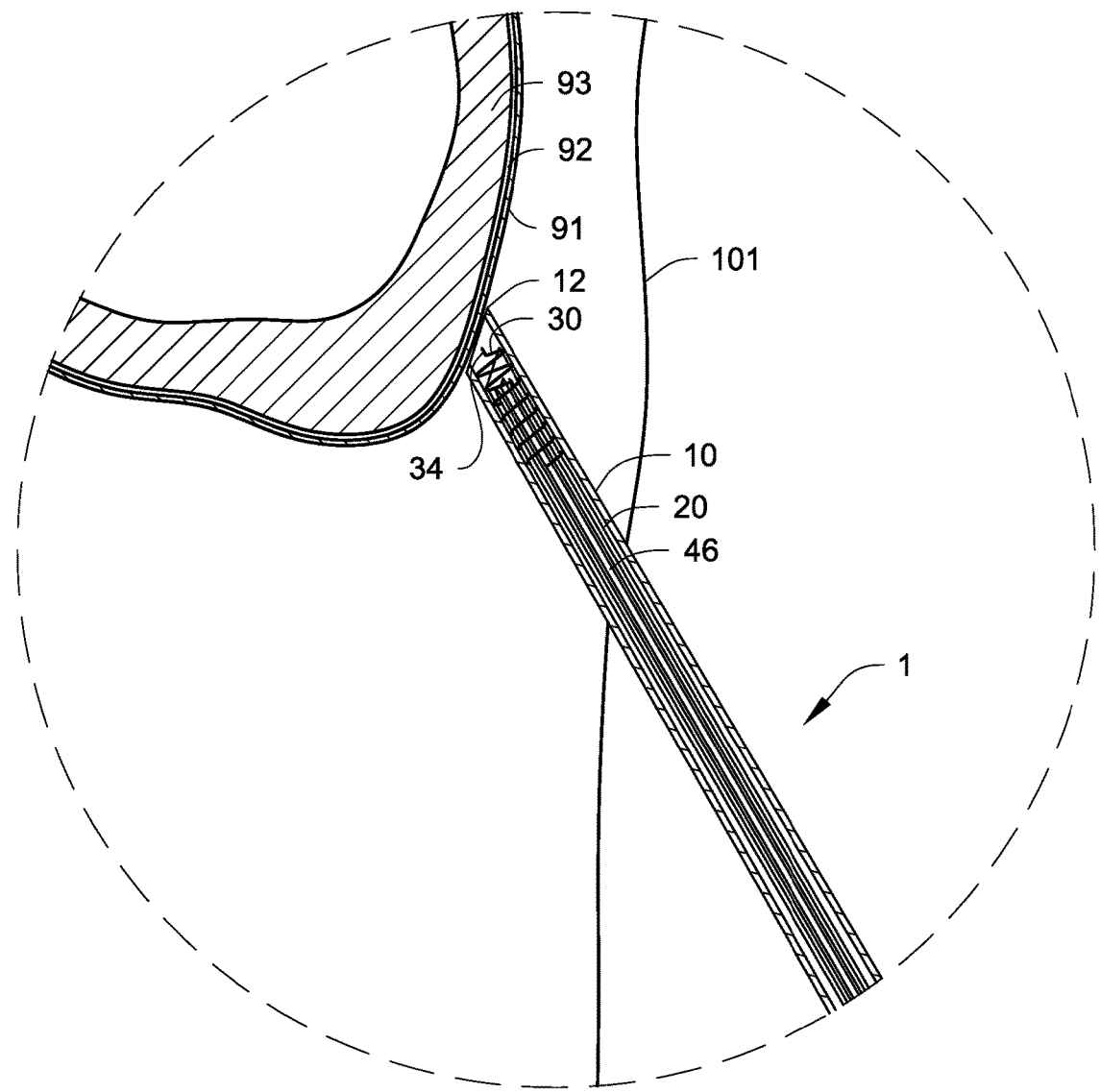
FIG. 7B is a diagram according to another embodiment showing the distal end of the medical device inserted into the body cavity and touching the pericardium.

FIG. 7A is a diagram according to one embodiment showing the distal end (12) of the medical device (1) inserted through the body wall (101) and touching the pericardium (91). FIG. 7B is a diagram according to another embodiment showing the distal end (12) of the medical device (1) inserted through the body wall (101) and touching the pericardium (91). The inner tubular body (20) is shown at the first position, and the tissue engagement member (30) is retracted inside the medical device (1). The medical device is not inserted into the pericardium (91), pericardial space (92), and myocardium (93) in these figures. The delivery mechanisms are shown at the third position and are retracted inside the medical device (1).

Figure 8A:
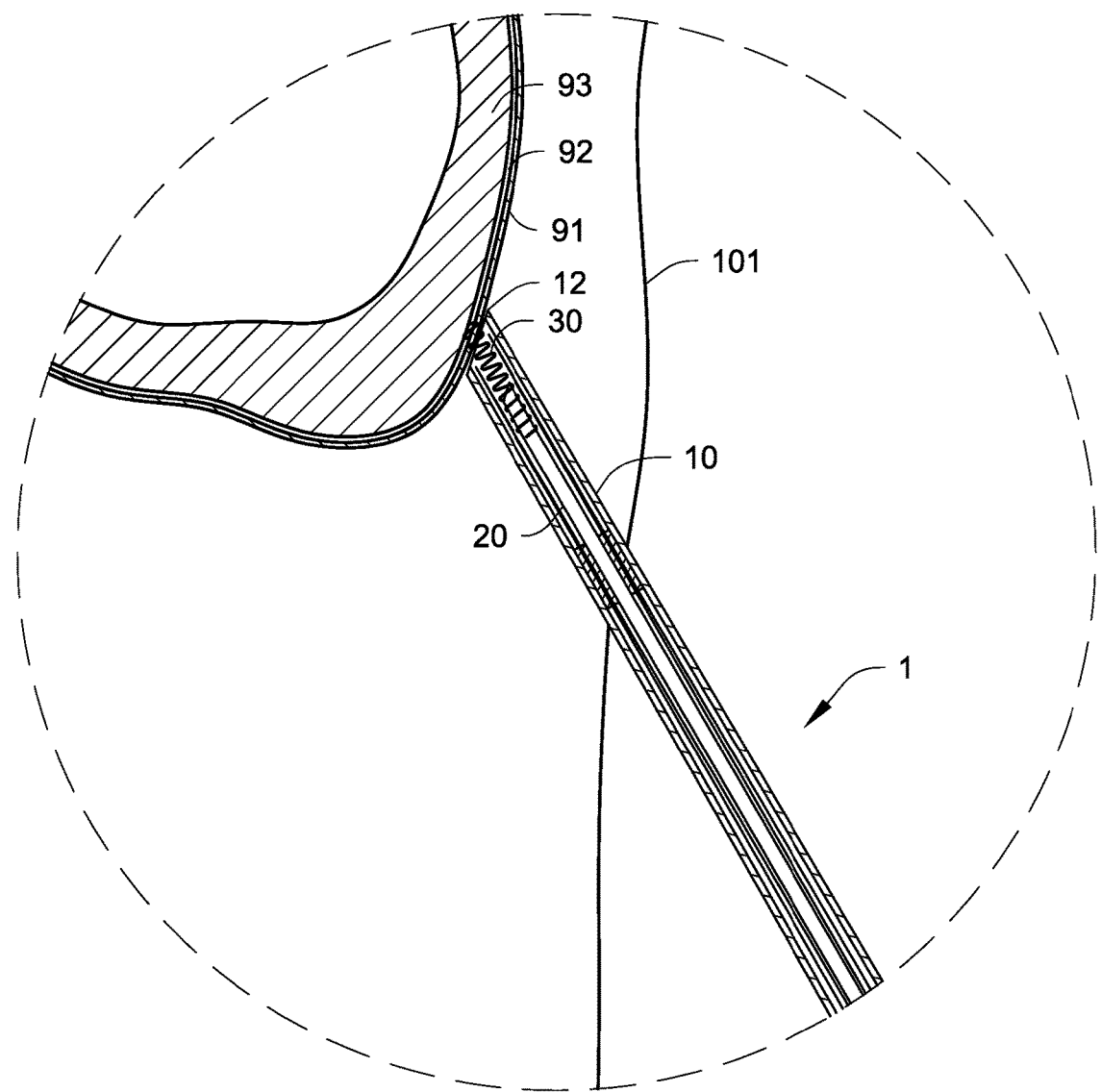
FIG. 8A is a diagram according to one embodiment showing the distal end of the medical device inserted into the body cavity.
Figure 8B:
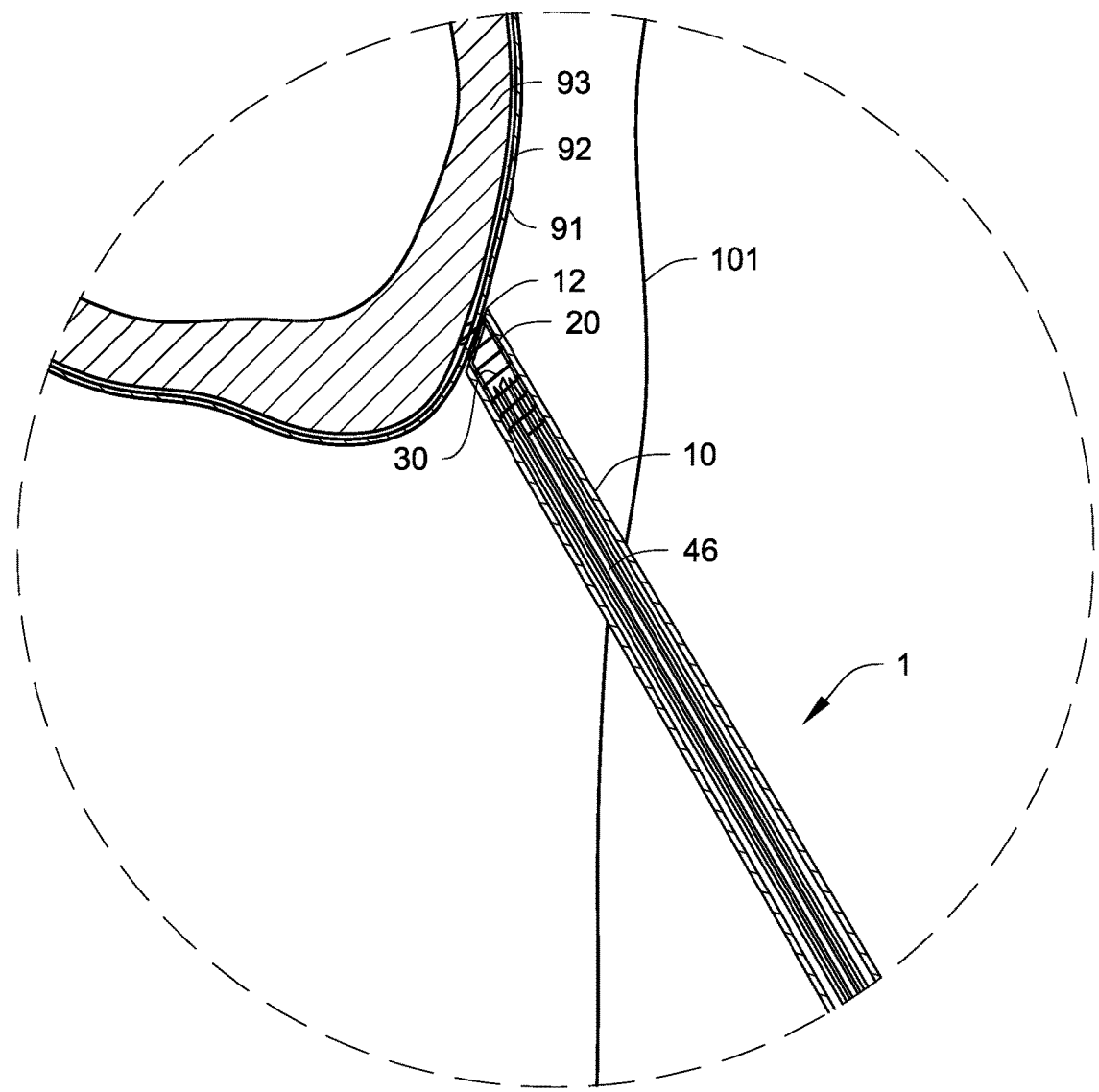
FIG. 8B is a diagram according to another embodiment showing the distal end of the medical device inserted into the body cavity.

FIG. 8A is a diagram according to one embodiment showing the distal end of the medical device (1) inserted through the body wall (101) and touching the pericardium (91). FIG. 8B is a diagram according to another embodiment showing the distal end of the medical device (1) inserted through the body wall (101) and touching the pericardium (91). The helical tissue engagement member (30) is engaged with the pericardium (91) in these figures. The helical tissue engagement member (30) may reach the pericardial space (92) and the myocardium (93). The inner tubular body (20) is shown at the second position. The delivery mechanisms are shown at the third position and are retracted inside the medical device (1).

Figure 9A:
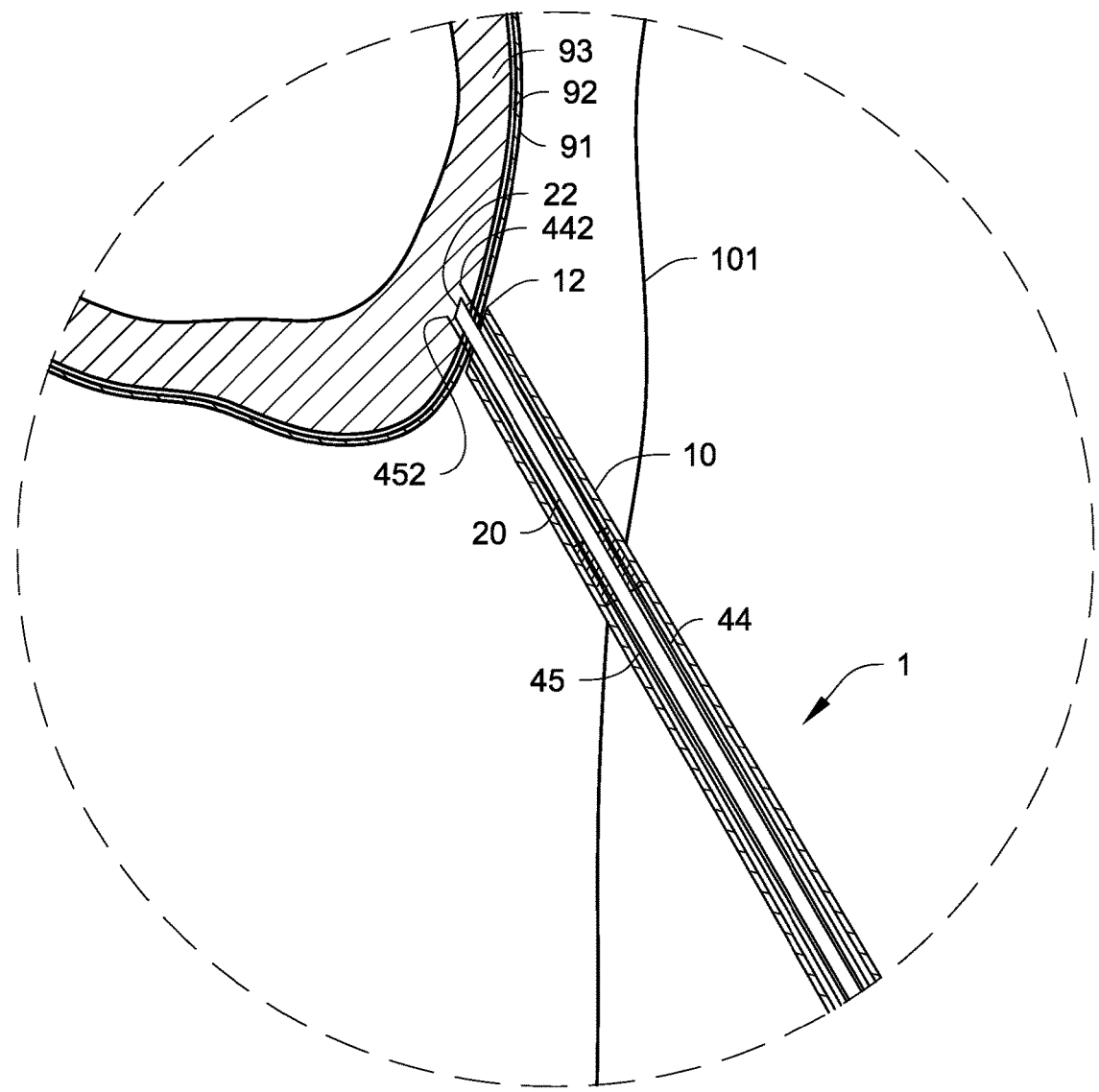
FIG. 9A is a diagram according to one embodiment showing the distal end of the medical device inserted into the body cavity. Tissue engagement member is not shown.
Figure 9B:
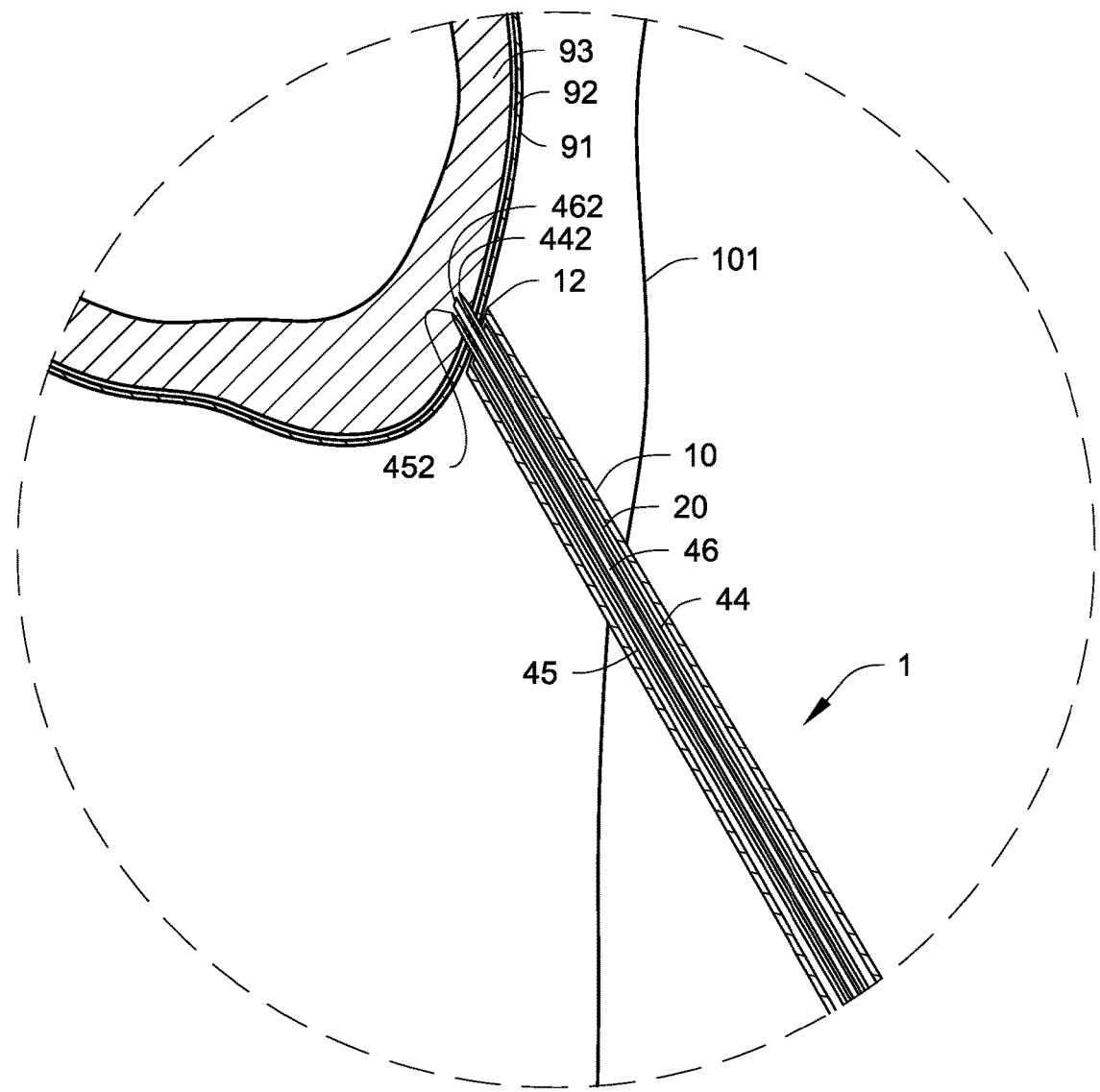
FIG. 9B is a diagram according to another embodiment showing the distal end of the medical device inserted into the body cavity. The helical tissue engagement member is not shown.

FIG. 9A is a diagram according to one embodiment showing the distal end (12) of the medical device (1) inserted through the body wall (101) and touching the pericardium (91). The inner tubular body (20) and two needles (44 and 45) are at the fourth position and the tips of the inner tubular body (22) and two needles (442 and 452) are inserted into the pericardial space (92) and the myocardium (93). FIG. 9B is a diagram according to another embodiment showing the distal end (12) of the medical device (1) inserted through the body wall (101) and touching the pericardium (91) The center tubular body (46) and two needles (44 and 45) are at the fourth position and tips of the center tubular body (462), and two needles (442 and 452) are inserted into the pericardial space (92) and myocardium (93). The tissue engagement member is not shown in these figures.

Figure 10:
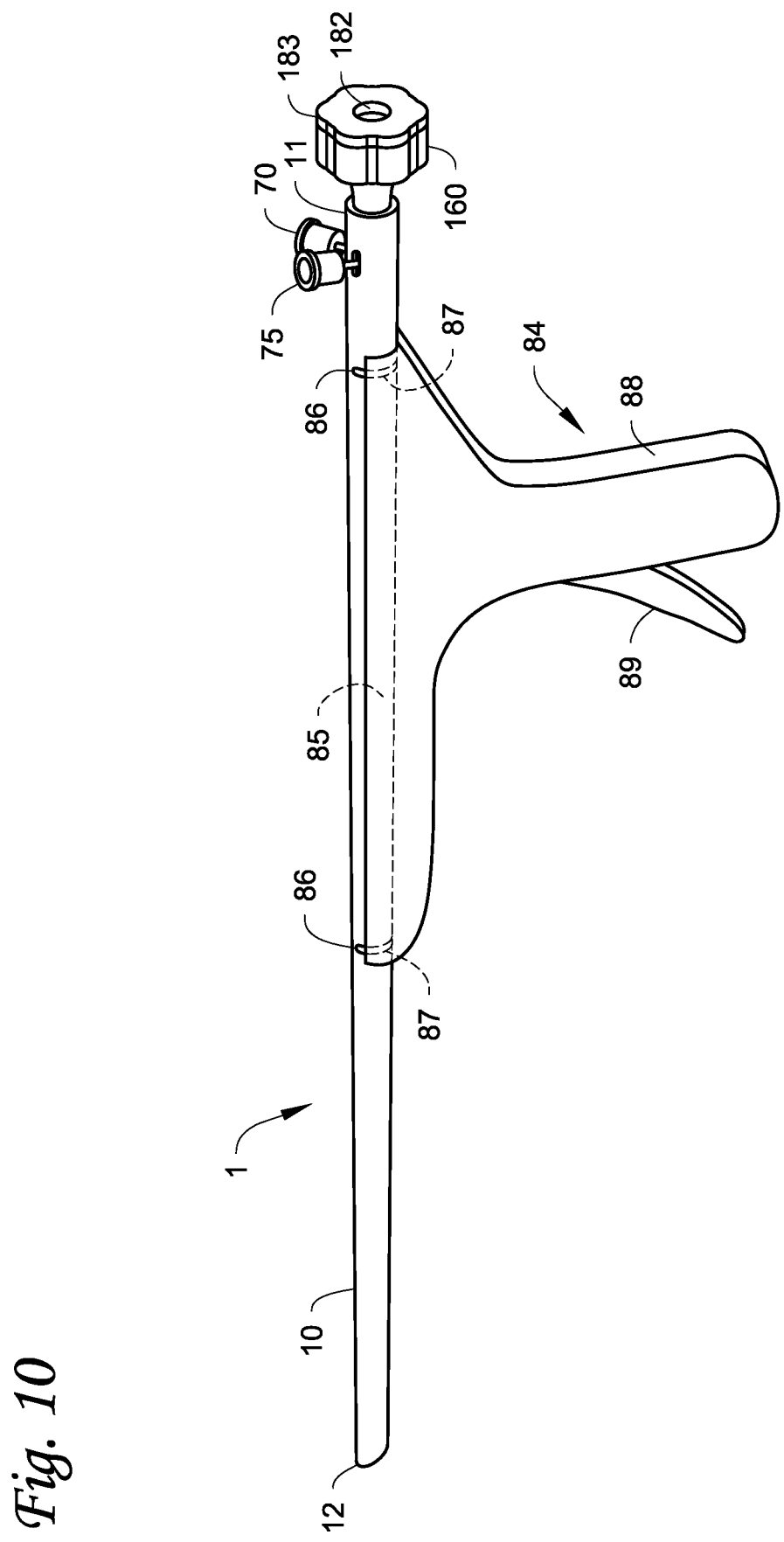
FIG. 10 is a side-proximal isometric view of the medical device according to one embodiment attached to a holder.

FIG. 10 is a side-proximal isometric view of the medical device attached to a holder according to one embodiment. The medical device (1) can be attached to a holder (84) for ergonomic use. The holder (84) has a device-receiving part (85), a handle (88) and a trigger (89). The device-receiving part (85) has the same contour as the outer surface of the outer tubular body (10) and protrusions (87) that engage with the pre-formed threads (86) on the side of the outer tubular body (10). The medical device (1) can be snapped into the device-receiving part (85) of the holder (84) and released by pulling the trigger (89).

A method for treating or monitoring a patient suffering from a cardiac includes delivering one or more agents and/or modalities directly to the heart of the subject including the myocardium and the pericardial space. Such agents and/or modalities include, but are not limited to, medicament, growth factors, cells, electrical current, voltage, and an electric signal. When more than one agents and/or modalities are delivered, the first agent or modality and the one or more further agents and/or modalities can be delivered simultaneously or sequentially to the same area of the patient's heart. The medical device (1) can be used for such direct delivery to the patient's heart (90).

The method of using the medical device (1) and treating or monitoring a patient suffering from a cardiac condition is disclosed. The method includes inserting the first distal end (12) of the medical device (1) with the inner tubular body (20) at the first position into a body cavity of a patient as shown in FIG. 6. The method also includes operating the medical device (1) so that the first distal end (12) of the medical device (1) comes in contact with a pericardium (91) of the patient as shown in FIGS. 7A and 7B. The method also includes penetrating the pericardium (91) using the tip (34) of the helical tissue engagement member (30) as shown in FIGS. 8A and 8B. The method also includes rotating the inner tubular body (20) in the first direction so that the helical tissue engagement member (30) enters the pericardial space (92) and the myocardium (93). The method also includes locating the inner tubular body (20) to the second position. The method also includes moving the delivery mechanism such as needle 1 (44) or needle 2 (45) from the third position (the retracted position) to the fourth position (the exposed position) as shown in FIGS. 9A and 9B. The method also includes delivering the one or more agents and/or modalities to the myocardium (93) sequentially or simultaneously. The method also includes releasing the medical device (1) from the patient by turning the helical tissue engagement member (30) in the second direction. The method also includes removing the medical device (1) from the patient.

When two or more agents and/or modalities are to be delivered sequentially to the heart using the medical device (1), the medical device (1) can be left attached to the cardiac muscle via the helical tissue engagement member (30) during the delivery of the first agent or modality and during the delivery of the one or more further agents and/or modalities, and the medical device (1) can stay connected to the heart (90) between the delivery of the first agent or modality and the delivery of the one or more further agents and/or modalities.

Alternatively, when two or more agents and/or modalities are delivered simultaneously to the heart (90) using the medical device (1), more than one delivery mechanism can be advanced to the fourth position (the exposed position) while the medical device (1) is attached to the pericardium (91) or myocardium (93) via the helical tissue engagement member (30).

Examples

Hereinafter, a further detailed description of the medical device according to several different embodiments and the method of treating patients will be given. However, it should be appreciated that the present disclosure is not limited to the embodiment shown below.

In operation, the materials for the medical device (1) can be any material suitable for medical uses. In one example, outer tubular body (10) and inner tubular body (20) are made of type 316 stainless steel hypodermic tubing (H316). In one example, the helical tissue engagement member (30) is made of AISI 304 alloy. In one example, the spring (55) that is configured to control the movement of the inner tubular body (20) is made of MP35N or similar alloy. In one example, the spring is made of biocompatible material with about 0.8 mm-about 1.1 mm spacing between each helical ring. In one example, the center tubular body (46) is made of AISI316 or similar alloy. The abovementioned materials can be replaced with other surgically compatible materials used for similar purposes.

In operation, the first distal end (12) of the outer tubular body (10) can have a cutting edge (16), and can be beveled, so that the point has an angle between about 10° and about 70° relative to the first longitudinal axis of the outer tubular body (13).

In one embodiment, the second distal end (22) of the inner tubular body (20) is configured to form a tight seal when the tissue engagement member (30) is engaged with the heart (90). A port that allows passage of the delivery mechanism without breaking the seal formed between the heart (90) can be disposed at the second distal end (22) of the inner tubular body (20). The port can be made of an elastic material and is configured to allow passage of delivery mechanism without breaking the seal formed between the second distal end (22) of the inner tubular body (20) and the heart (90).

In operation, the tissue engagement member (30) can be a spring, and a short tip (34) can have a blunt end, which is configured to be able to penetrate the pericardium, but not to unintentionally penetrate the myocardium (93). The tissue engagement member (30) is corkscrew-shaped: when it is rotated to the first direction, it advances into the heart (90), and when it is rotated to the second direction, it comes out of the heart. This movement of the tissue engagement member (30) secures the medical device (1) onto the heart (90) and aids in forming a seal between the inner tubular body (20) and the heart (90).

In operation, the gear (50) is configured to control the movement of the inner tubular body (20), and the mechanism can be any designs configured to provide a similar rotational movement to the inner tubular body (20). In the example shown in FIG. 3A, protrusions (18) formed on the outer surface of the inner tubular body (20) engages with a helical groove (52) formed on the inner surface of the gear (50) and guides its rotational movement. In the example shown in FIG. 3C, protrusions (17) formed on the inner surface (14) of the outer tubular body (10) engages with a helical groove (51) formed on the periphery of the gear (50) and guides the rotational movement of the inner tubular body (20).

In operation, when the gear (50) is rotated to the first direction, the combined inner tubular body (20) and tissue engagement member (30) unit advances and tissue engagement member (30) is exposed from the distal end (12) of the outer tubular body (10). When the gear (50) is rotated to the second direction, the combined inner tubular body (20) and tissue engagement member (30) unit retracts into the outer tubular body (10). The helical grooves (51 and 52) are configured so that the rotation of the inner tubular body (20) is limited to a predetermined angle, for example, to about 1080°, so that the distance that the tissue engagement member (30) can advance is limited to a predetermined length. This can reduce the risk of unintentional or accidental overturning, which can cause unintended puncture of the heart (90). In operation, the range of rotation angle can be adjusted according to the tissues to be targeted.

In operation, the rotation and advancement of the inner tubular body (20) can be activated by a thumb button (60). Thumb button (60) can be connected with a spring (55), and configured so that operation of the thumb button allows rotation of the inner tubular body (20) to the first direction by a predetermined angle. For example, one pushing of the thumb button (60) can trigger about 90° rotation of the inner tubular body (20) to the first direction and advance the tissue engagement member (30) by a predetermined distance. The total number of allowable advancement can be limited, for example, to about 12 times, so that the rotation of the combined inner tubular body (20) and tissue engagement member (30) unit is limited to about 1080°. This mechanism can allow the operator to precisely control the depth the tissue engagement member (30) is inserted and can reduce the risk of unintentional puncture of the heart (90). The tissue engagement member (30) can be released from the tissue by turning the tissue engagement member (30) to a second direction.

In operation, a variety of mechanical designs can be used to cause rotational movement of the inner tubular body (20). In one embodiment, a torsional hub (not shown) can be disposed on the medical device (1). The torsional hub can be turned manually by the user to advance and retract the tissue engagement member (30). The turning of the torsional hub can be limited to predetermined number of turns or a predetermined angle by molded stops formed on the gear (50).

In another embodiment, a spring-loaded button (not shown) with a gear mechanism (not shown) can be used. For example, the button can be configured so that each actuation of the button causes a rotation of the inner tubular body (20) by a predetermined angle, for example about 90°, and the degree of rotation can be controlled by the number the button is depressed, for example, maximum of about 12 times.

In yet another embodiment, a pre-loaded torsional spring (not shown) can be used to rotate the combined inner tubular body (20) and tissue engagement member (30) unit. In this embodiment, actuation of the thumb button (60) triggers rotation of the inner tubular body (20) by the torsional spring, until the rotation is stopped by the end of the helical grooves (51 and 52), for example after rotating about 1080°. This design allows "manual reloading" of the torsional spring by rotating the attached torsional hub relative to the device body.

In operation, further different mechanisms to control rotation are possible, for example, by an electromechanical means configured to drive the gears to rotate in a desired angle.

In operation, the tip (34) of the tissue engagement member (30) can be designed so that a full depression of the spring-loaded thumb button (60) results in full extension of the tip (34) into the pericardial space (92). Upon release of the thumb button (60), excess clearances needed for rotation are eliminated and engagement of the gear (50) occur, thereby resulting in a slight retraction of the tip (34) from the full extension seen when the thumb button (60) is fully depressed.

In the examples shown in FIGS. 4B and 5B, needle 1 (44) is coupled to a sideport (70). In operation, the sideport (70) is used as an entry site for agents and/or modalities and as a knob to move the needle 1 (44). The slit 1 (71) formed in the outer tubular body (10) limits the movement of sideport (70) to positions between the proximal end (72) of the slit 1 (71) and the distal end (73) of the slit 1 (71). The sideport (70) being at the proximal end (72) of the slit 1 (71) corresponds to the third position of the delivery mechanism, and the sideport (70) being at the distal end (73) of slit 1 (71) corresponds to the fourth position of the delivery mechanism. The medical device (1) can house more than one delivery mechanism inside the inner tubular body (20), and more than one delivery mechanism can be used simultaneously or sequentially.

In operation, the delivery mechanism can be one or more selected from a needle, a catheter, a guide-wire, mapping electrodes, leads, and a camera including a chip-based catheter camera. The delivery mechanisms are configured to perform procedures including injection of agents and/or modalities into the heart, electrical stimulation of the heart, monitoring voltage and current in the heart, and direct imaging of the heart. When delivery of multiple agents and/or modalities is desired, the tissue engagement member (30) can anchor the medical device (1) in place while multiple agents and/or modalities can be simultaneously or sequentially delivered.

In operation, the delivery mechanism and the inner tubular body (20) can be connected to an external plunger device or an external pump, which can have programming capabilities.

Method of Treatment

The following describes a method of treating or monitoring a patient suffering from a cardiac condition.

When the agents and/or modalities are directly delivered to the heart of a patient suffering from a cardiac condition, the agents and/or modalities will take effect immediately and is beneficial for the patient. For example, in cardiac conditions that require immediate intervention such as cardiac arrest or cardiac ischemia, direct delivery method has significant advantage over others, because the agents and/or modalities reach the target tissue immediately and the delivery method does not require that agents and/or modalities are delivered to the heart by a blood flow. Similarly, in a regenerative therapy of a damaged myocardium, direct delivery method is advantageous, because the agents and/or modalities can be targeted to the infarct area and their delivery does not rely on blood flow, which is often lost or reduced when the myocardium is damaged. Such agents and/or modalities include medicament, growth factors, cells, electrical current, voltage, or an electric signal.

In operation, it can be beneficial to apply multiple agents and/or modalities to the same area of the heart. For example, the target area can be primed by injection of a medicament, and the same area can be injected with a second medicament or cells. In yet another embodiment, a medicament can be applied and later monitored or stimulated by an electrode. In another embodiment, the heart activity can be monitored first and injected later with another agents and/or modalities. The combination and the order these agents and/or modalities are applied are not limited to these embodiments and can be done in any combinations and orders.

In operation, the application of agents and/or modalities can be done using the medical device (1). The agents and/or modalities can be delivered through the delivery mechanisms. The flow of agents and/or modalities can be either from medical device (1) to the heart or from the heart to the medical device (1), and the flow of agents and/or modalities is reversible. The agents and/or modalities can be delivered at the simultaneously or sequentially. That is, for example, a medicament can be delivered through the delivery mechanism, while saline can be delivered through the inner tubular body (20). In one example, when an affected area requires washing before delivery of medicaments, the medical device (1) can be first secured onto the heart (90) using the tissue engagement member (30); next the affected area can be washed with several changes of saline passed through the inner tubular body (20), and then a medicament can be delivered through delivery mechanism to the washed area. During the washing and delivery process described above, the medical device (1) can remain attached to the heart via the tissue engagement member (30) and can assure that the same affected area is treated.

Although the present disclosure has been described with reference to preferred embodiments, those skilled in the art would recognize that various modifications can be made in form and detail, all without departing from the spirit and scope of the present disclosure. Those skilled in the art would also recognize that the medical device can be used for direct delivery into organs other than heart.

Aspects

The medical device of the present application has following aspects and obvious variations thereof. It is noted that any one of aspects 1-17, 24, and 25 below can be combined with any one of aspects 18-23.

[Aspect 1] A medical device for delivering an agent and/or a modality to an organ comprising:

an outer tubular body comprising a first proximal end, a first distal end, a first lumen extending between the first proximal end and the first distal end, and a first longitudinal axis extending from the first proximal end to the first distal end;

an inner tubular body comprising a second proximal end, a second distal end, a second lumen extending between the second proximal end and the second distal end, and a second longitudinal axis extending from the second proximal end to the second distal end, the inner tubular body movably disposed in the first lumen of the outer tubular body, the second proximal end of the inner tubular body operably coupled to the first proximal end of the outer tubular body, and the inner tubular body displaceable along the first longitudinal axis of the outer tubular body from a first position to a second position; and a tissue engagement member comprising a third proximal end, a third distal end, and a third longitudinal axis extending from the third proximal end to the third distal end, the tissue engagement member attached to the second distal end of the inner tubular body, the third longitudinal axis of the tissue engagement member substantially parallel to or overlapping with the first longitudinal axis of the outer tubular body and the second longitudinal axis of the inner tubular body, the tissue engagement member being in the first lumen of the outer tubular body, the third distal end of the tissue engagement member recessed relative to the first distal end of the outer tubular body when the inner tubular body is at the first position, and the third distal end of the tissue engagement member extending out of the first distal end of the outer tubular body when the inner tubular body is at the second position.

[Aspect 2] The medical device according to aspect 1, further comprising:
  at least one delivery mechanism having a fourth proximal end and a fourth distal end;
    the at least one delivery mechanism located in the first lumen of the outer tubular body,
    the at least one delivery mechanism operably coupled to the outer tubular body,
    the at least one delivery mechanism displaceable along the first longitudinal axis of the outer tubular body from a third position to a fourth position,
    the fourth distal end of the at least one delivery mechanism recessed relative to the first distal end of the outer tubular body when the at least one delivery mechanism is at the third position, and
    the fourth distal end of the at least one delivery mechanism extending out of the first distal end of the outer tubular body when the at least one delivery mechanism is at the fourth position.

[Aspect 3] The medical device according to any one of aspect 1 or aspect 2, wherein
  the outer tubular body is made of stainless steel,
  the outer diameter of the outer tubular body increases from the first distal end towards the first proximal end, and
  the first distal end of the outer tubular body is beveled.

[Aspect 4] The medical device according to any one of aspects 1-3, further comprising
  a center port, wherein
    the center port is attached to the second distal end of the inner tubular body and
    the center port has an opening.

[Aspect 5] The medical device according to any one of aspects 1-4, further comprising:
  a tip attached to the third distal end of the tissue engagement member, wherein
  a free end of the tip is blunt.

[Aspect 6] The medical device according to any one of aspects 1-5, further comprising a gear, wherein
  the gear is configured to control the movement of the inner tubular body.

[Aspect 7] The medical device according to any one of aspects 1-6, wherein
  when the inner tubular body is rotated in a first direction around the second longitudinal axis, the inner tubular body and the tissue engagement member move towards the first distal end of the outer tubular body, and
  when the inner tubular body is rotated in a second direction around the second longitudinal axis, the inner tubular body and the tissue engagement member move towards the first proximal end of the outer tubular body.

[Aspect 8] The medical device according to any one of aspects 1-7 further comprising:
  a spring; and
  a thumb button, wherein
    the spring is configured to control a movement of the inner tubular body, and
    the thumb button is configured to control a movement of the spring.

[Aspect 9] The medical device according to any one of aspects 1-8, wherein
  a rotatable range of the inner tubular body relative to the outer tubular body is limited to a first predetermined angle, and
  an operation of the thumb button allows a rotation of the inner tubular body relative to the outer tubular body by a second predetermined angle.

[Aspect 10] The medical device according to any one of aspects 1-9, wherein
  the at least one delivery mechanism include a needle, a catheter, a tube, a guide-wire, mapping electrodes, leads, and a camera.

[Aspect 11] The medical device according to any one of aspects 1-10, wherein
  the at least one delivery mechanism include at least two delivery mechanisms.

[Aspect 12] The medical device according to any one of aspects 1-11, wherein
  the at least two delivery mechanisms are exclusively used.

[Aspect 13] The medical device according to any one of aspects 1-11, wherein the at least two delivery mechanisms are simultaneously used.

[Aspect 14] The medical device according to any one of aspects 1-13 further comprising a sideport operably coupled to the outer tubular body, wherein
  the at least one delivery mechanism is configured to move between the third position and the fourth position by operating the sideport or the thumb button, and
  the side port is configured to be a conduit for delivering the agent and/or the modality supplied through the side port and dispensed from the fourth distal end of the at least one delivery mechanism.

[Aspect 15] The medical device according to any one of aspects 1-14, further comprising a stopcock attached to the sideport, wherein
  the stopcock is configured to prevent air leakage, and
  the stopcock is configured to connect a syringe.

[Aspect 16] The medical device according to any one of aspects 1-15, further comprising a plunger configured to control injection of the agent and/or the modality.

[Aspect 17] The medical device according to any one of aspects 1-16, wherein the agent and/or the modality include a medicament, a gel, a growth factor, a cell, an electrical current, a voltage, or an electric signal.

[Aspect 18] A method for treating or monitoring a patient suffering from a cardiac condition comprising:
  delivering one or more agents and/or the modalities directly to a cardiac muscle of the patient in need thereof.

[Aspect 19] The method of aspect 18, wherein
  the one or more agents and/or the modalities include a first agent or the modality and one or more further agents and/or the modalities,
  the first agent or the modality and the one or more further agents and/or the modalities are delivered simultaneously or sequentially, and
  an area that receives the first agent or the modality and an area that receives the one or more further agents and/or the modalities substantially overlap.

[Aspect 20] The method of any one of aspect 18 or aspect 19, wherein the first agent or the modality and the one or more further agents and/or the modalities include a medicament, a gel, a growth factor, a cell, an electrical current, a voltage, or an electric signal.

[Aspect 21] The method according to any one of aspects 18-20, wherein delivering one or more agents and/or modalities directly to a cardiac muscle of a patient in need thereof includes delivering of one or more agents and/or modalities using the medical device according to any one of aspects 1-17.

[Aspect 22] The method according to aspect 21, further comprising:
  inserting the first distal end of the medical device with the inner tubular body at the first position into a body cavity of a patient;
  operating the medical device such that the first distal end of the medical device is in contact with a pericardium of the patient;
  penetrating the pericardium using the tip of the tissue engagement member;
  rotating the inner tubular body in a first direction so as to engage the tissue engagement member with a heart of a patient;
  locating the inner tubular body to the second position;
  delivering the one or more agents and/or modalities to the cardiac muscle;
  releasing the medical device from the patient by turning the tissue engagement member in a second direction; and
  removing the medical device from the patient.

[Aspect 23] The method according to any one of aspects 21-22, wherein
  the medical device is attached to the cardiac muscle via the tissue engagement member during a delivery of the first agent or modality and during a delivery of the one or more further agents and/or modalities, and
  the medical device is not released from the cardiac muscle between the delivery of the first agent or modality and the delivery of the one or more further agents and/or modalities.

[Aspect 24] The medical device according to any one of aspects of 1-17, wherein the first longitudinal axis of the outer tubular body, the second longitudinal axis of the inner tubular body, and the third longitudinal axis of the tissue engagement member are substantially parallel.

[Aspect 25] The medical device according to any one of aspects of 1-17 and 24, wherein the first longitudinal axis of the outer tubular body, the second longitudinal axis of the inner tubular body, and the third longitudinal axis of the tissue engagement member overlap.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, indicate the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts, without departing from the scope of the present disclosure. The word "embodiment" as used within this specification may, but does not necessarily, refer to the same embodiment. This specification and the embodiments described are examples only. Other and further embodiments may be devised without departing from the basic scope thereof, with the true scope and spirit of the disclosure being indicated by the claims that follow.

What is claimed is:

1. A medical device for delivering an agent and/or a modality to an organ, the device comprising:
  an outer tubular body comprising a first proximal end, a first distal end, a first lumen extending between the first proximal end and the first distal end, and a first longitudinal axis extending from the first proximal end to the first distal end;
  an inner tubular body comprising a second proximal end, a second distal end, a second lumen extending between the second proximal end and the second distal end, and a second longitudinal axis extending from the second proximal end to the second distal end,
    the inner tubular body movably disposed in the first lumen of the outer tubular body,
    the second proximal end of the inner tubular body operably coupled to the first proximal end of the outer tubular body, and
    the inner tubular body displaceable along the first longitudinal axis of the outer tubular body from a first position to a second position;
  a tissue engagement member comprising a third proximal end, a third distal end, and a third longitudinal axis extending from the third proximal end to the third distal end,
    the tissue engagement member being attached to the second distal end of the inner tubular body,
    the tissue engagement member being helically shaped and being configured to move in a corkscrew-like movement when the inner tubular body is rotated around the second longitudinal axis,
    the tissue engagement member being configured to penetrate into a target tissue and to anchor the medical device onto the target tissue by the corkscrew-like movement when the tissue engagement member is rotated around the second longitudinal axis,
    the tissue engagement member being in the first lumen of the outer tubular body, the third distal end of the tissue engagement member being recessed relative to the first distal end of the outer tubular body when the inner tubular body is at the first position, and the third distal end of the tissue engagement member extending out of the first distal end of the outer tubular body when the inner tubular body is at the second position,
    wherein the third longitudinal axis of the tissue engagement member is substantially parallel to the first longitudinal axis of the outer tubular body and the second longitudinal axis of the inner tubular body when the inner tubular body is at the first position, the second position, and a position between the first position and the second position; and
  at least one delivery mechanism having a fourth proximal end and a fourth distal end,
    the at least one delivery mechanism being located in the first lumen of the outer tubular body,
    the at least one delivery mechanism being operably coupled to the outer tubular body,
    the at least one delivery mechanism being displaceable along the first longitudinal axis of the outer tubular body from a third position to a fourth position,
    the fourth distal end of the at least one delivery mechanism being recessed relative to the first distal end of the outer tubular body when the at least one delivery mechanism is at the third position,
    the fourth distal end of the at least one delivery mechanism being configured to extend out of the first distal end of the outer tubular body when the at least one delivery mechanism is at the fourth position.

2. The medical device according to claim 1, wherein
the outer tubular body is made of stainless steel,
the outer diameter of the outer tubular body increases from the first distal end towards the first proximal end, and
the first distal end of the outer tubular body is beveled.

3. The medical device according to claim 1, further comprising:
a tip attached to the third distal end of the tissue engagement member, wherein
a free end of the tip is blunt.

4. The medical device according to claim 1, further comprising a gear, wherein
the gear is configured to control the movement of the inner tubular body,
a rotatable range of the gear relative to the outer tubular body being limited to a first predetermined angle.

5. The medical device according to claim 4, wherein
when the inner tubular body is rotated in a first direction around the second longitudinal axis, the inner tubular body and the tissue engagement member move towards the first distal end of the outer tubular body, and
when the inner tubular body is rotated in a second direction around the second longitudinal axis, the inner tubular body and the tissue engagement member move towards the first proximal end of the outer tubular body.

6. The medical device according to claim 5 further comprising:
a spring; and
a thumb button, wherein
the spring is configured to control a movement of the inner tubular body, and
the thumb button is configured to control a movement of the spring.

7. The medical device according to claim 6, wherein
a rotatable range of the inner tubular body relative to the outer tubular body is limited to a first predetermined angle, and
an operation of the thumb button allows a rotation of the inner tubular body relative to the outer tubular body incrementally.

8. The medical device according to claim 1, wherein
the at least one delivery mechanism include at least one selected from the group consisting of a needle, a catheter, a tube, a guide-wire, mapping electrodes, leads, and a camera.

9. The medical device according to claim 1 further comprising a side port operably coupled to the outer tubular body, wherein
the at least one delivery mechanism is configured to move between the third position and the fourth position by operating the side port,
the side port is configured to be a conduit for delivering the agent and/or the modality supplied through the side port and dispensed from the fourth distal end of the at least one delivery mechanism.

10. The medical device according to claim 9, further comprising a stopcock attached to the side port, wherein
the stopcock is configured to prevent air leakage, and
the stopcock is configured to connect a syringe.

11. The medical device according to claim 1, wherein the agent and/or the modality include a medicament, a gel, a growth factor, a cell, an electrical current, a voltage, or an electric signal.

12. The medical device according to claim 1, further comprising:
a center luer lock, wherein
a lumen of the center luer lock is continuous with the second lumen of the inner tubular body or with a lumen of the at least one delivery mechanism,
the center luer lock is configured to be a conduit for delivering the agent and/or the modality supplied through the center luer lock and dispensed from the second distal end of the inner tubular body or the fourth distal end of the at least one delivery mechanism, and
the center luer lock is configured to receive a stopcock.

13. A method for treating or monitoring a patient suffering from a cardiac condition comprising:
delivering one or more agents and/or modalities directly to a cardiac muscle of the patient in need thereof using the medical device according to claim 1.

14. The method of claim 13, wherein
the one or more agents and/or the modalities include a first agent or the modality and one or more further agents and/or the modalities,
the first agent or the modality and the one or more further agents and/or the modalities are delivered simultaneously or sequentially, and
an area that receives the first agent or the modality and an area that receives the one or more further agents and/or the modalities substantially overlap.

15. The method of claim 13, wherein the one or more agents and/or modalities include a medicament, a gel, a growth factor, a cell, an electrical current, a voltage, or an electric signal.

16. The method according to claim 13, further comprising:
inserting the first distal end of the medical device with the inner tubular body at the first position into a body cavity of a patient;
operating the medical device such that the first distal end of the medical device is in contact with a pericardium of the patient;
penetrating the pericardium using the tip of the tissue engagement member;
rotating the inner tubular body in a first direction so as to engage the tissue engagement member with a heart of a patient;
locating the inner tubular body to the second position;
delivering the one or more agents and/or modalities to the cardiac muscle;
releasing the medical device from the patient by turning the tissue engagement member in a second direction; and
removing the medical device from the patient.

17. The method according to claim 14, wherein
the medical device is attached to the cardiac muscle via the tissue engagement member during a delivery of the first agent or modality and during a delivery of the one or more further agents and/or modalities, and
the medical device is not released from the cardiac muscle between the delivery of the first agent or modality and the delivery of the one or more further agents and/or modalities.

18. A medical device for delivering an agent and/or a modality to an organ, the device comprising:
- an outer tubular body comprising a first proximal end, a first distal end, a first lumen extending between the first proximal end and the first distal end, and a first longitudinal axis extending from the first proximal end to the first distal end, wherein
  - the outer diameter of the outer tubular body increases from the first distal end towards the first proximal end, and,
  - the first distal end of the outer tubular body is beveled;
- an inner tubular body comprising a second proximal end, a second distal end, a second lumen extending between the second proximal end and the second distal end, and a second longitudinal axis extending from the second proximal end to the second distal end, wherein
  - the inner tubular body movably disposed in the first lumen of the outer tubular body,
  - the second proximal end of the inner tubular body operably coupled to the first proximal end of the outer tubular body,
  - the inner tubular body displaceable along the first longitudinal axis of the outer tubular body from a first position to a second position;
- a tissue engagement member comprising a third proximal end, a third distal end, and a third longitudinal axis extending from the third proximal end to the third distal end, wherein
  - the tissue engagement member being attached to the second distal end of the inner tubular body,
  - the tissue engagement member being helically shaped and being configured to move in a corkscrew-like movement when the inner tubular body is rotated around the second longitudinal axis,
  - the tissue engagement member being configured to penetrate into a target tissue and to anchor the medical device onto the target tissue by the corkscrew-like movement when the tissue engagement member is rotated around the second longitudinal axis,
  - the tissue engagement member being in the first lumen of the outer tubular body, the third distal end of the tissue engagement member being recessed relative to the first distal end of the outer tubular body when the inner tubular body is at the first position, and the third distal end of the tissue engagement member extending out of the first distal end of the outer tubular body when the inner tubular body is at the second position,
  - wherein the third longitudinal axis of the tissue engagement member is substantially parallel to the first longitudinal axis of the outer tubular body and the second longitudinal axis of the inner tubular body when the inner tubular body is at the first position, the second position, and a position between the first position and the second position;
- a gear, wherein
  - the gear is configured to control the movement of the inner tubular body,
  - a rotatable range of the gear relative to the outer tubular body being limited to a first predetermined angle,
  - when the inner tubular body is rotated in a first direction around the second longitudinal axis, the inner tubular body and the tissue engagement member move towards the first distal end of the outer tubular body,
  - when the inner tubular body is rotated in a second direction around the second longitudinal axis, the inner tubular body and the tissue engagement member move towards the first proximal end of the outer tubular body,
  - a rotatable range of the inner tubular body relative to the outer tubular body is limited to a first predetermined angle;
- a spring, wherein
  - the spring is configured to control a movement of the inner tubular body;
- a thumb button, wherein
  - the thumb button is configured to control a movement of the spring,
  - an operation of the thumb button allows a rotation of the inner tubular body relative to the outer tubular body incrementally; and
- at least one delivery mechanism having a fourth proximal end and a fourth distal end,
  - the at least one delivery mechanism being located in the first lumen of the outer tubular body,
  - the at least one delivery mechanism being operably coupled to the outer tubular body,
  - the at least one delivery mechanism being displaceable along the first longitudinal axis of the outer tubular body from a third position to a fourth position,
  - the fourth distal end of the at least one delivery mechanism being recessed relative to the first distal end of the outer tubular body when the at least one delivery mechanism is at the third position,
  - the fourth distal end of the at least one delivery mechanism being configured to extend out of the first distal end of the outer tubular body when the at least one delivery mechanism is at the fourth position.

* * * * *